US008361787B2

(12) United States Patent
Lois-Caballe et al.

(10) Patent No.: US 8,361,787 B2
(45) Date of Patent: Jan. 29, 2013

(54) METHOD FOR EXPRESSION OF SMALL RNA MOLECULES WITHIN A CELL

(75) Inventors: Carlos Lois-Caballe, Cambridge, MA (US); David Baltimore, Pasadena, CA (US); Xiao-Feng Qin, Sugar Land, TX (US)

(73) Assignee: California Institute of Technology, Pasadena, CA (US)

( * ) Notice: Subject to any disclaimer, the term of this patent is extended or adjusted under 35 U.S.C. 154(b) by 191 days.

(21) Appl. No.: 12/795,581

(22) Filed: Jun. 7, 2010

(65) Prior Publication Data

US 2011/0059531 A1    Mar. 10, 2011

Related U.S. Application Data

(63) Continuation of application No. 10/243,816, filed on Sep. 13, 2002, now Pat. No. 7,732,193.

(60) Provisional application No. 60/322,031, filed on Sep. 13, 2001, provisional application No. 60/347,782, filed on Jan. 9, 2002, provisional application No. 60/389,592, filed on Jun. 18, 2002, provisional application No. 60/406,436, filed on Aug. 27, 2002.

(51) Int. Cl.
*C12N 15/00* (2006.01)
*C12N 15/88* (2006.01)
*C12Q 1/68* (2006.01)
*C12P 19/34* (2006.01)
*C07H 21/04* (2006.01)

(52) U.S. Cl. ...... 435/320.1; 435/6; 435/91.1; 435/91.31; 435/455; 536/23.1; 536/24.31; 536/24.5

(58) Field of Classification Search ............. 435/6, 91.1, 435/91.31, 320.1, 455; 536/23.1, 24.3, 24.5, 536/24.31; 514/44
See application file for complete search history.

(56) References Cited

U.S. PATENT DOCUMENTS

| | | | |
|---|---|---|---|
| 5,258,289 A | 11/1993 | Davis et al. | |
| 5,883,081 A | 3/1999 | Kraus et al. | |
| 6,022,962 A | 2/2000 | Chowrira et al. | |
| 6,060,317 A | 5/2000 | Malech | |
| 6,074,836 A | 6/2000 | Bordignon et al. | |
| 6,096,538 A | 8/2000 | Kingsman et al. | |
| 6,100,087 A | 8/2000 | Rossi et al. | |
| 6,218,186 B1 | 4/2001 | Choi et al. | |
| 6,255,071 B1 | 7/2001 | Beach et al. | |
| 6,274,788 B1 | 8/2001 | Kumar et al. | |
| 6,312,956 B1 | 11/2001 | Lane | |
| 6,482,618 B2 | 11/2002 | Mueller et al. | |
| 6,506,559 B1 | 1/2003 | Fire et al. | |
| 6,566,083 B1 | 5/2003 | Thastrup et al. | |
| 6,585,208 B1 | 7/2003 | Fraser | |
| 6,635,472 B1 | 10/2003 | Lauermann | |
| 6,664,107 B1 | 12/2003 | Mak et al. | |
| 7,195,916 B2 | 3/2007 | Qin et al. | |
| 7,732,193 B2 * | 6/2010 | Lois-Caballe et al. | 435/320.1 |
| 7,732,207 B2 | 6/2010 | Qin et al. | |
| 7,737,124 B2 | 6/2010 | Lois-Caballe et al. | |
| 7,919,309 B2 * | 4/2011 | Lois-Caballe et al. | 435/320.1 |
| 2003/0059944 A1 | 3/2003 | Lois-Caballe et al. | |
| 2003/0084471 A1 | 5/2003 | Beach et al. | |
| 2003/0124513 A1 | 7/2003 | McSwiggen | |
| 2003/0143742 A1 | 7/2003 | Lewis et al. | |
| 2003/0219823 A1 | 11/2003 | Alsobrook et al. | |
| 2010/0267146 A1 | 10/2010 | Lois-Caballe et al. | |

OTHER PUBLICATIONS

Ohkawa et al, Human Gene Therapy, vol. 11, pp. 577-585 (2000).*
Miyoshi et al, J. Virol., vol. 72, No. 10, pp. 8150-8157 (1998).*
Agrawal et al., "Antisense therapeutics: is it as simple as complementary base recognition?" Molecular Med. Today, vol. 6, pp. 72-81, 2000.
Arendt et al., "Vector systems for the delivery of small interfering RNAs: managing the RISC**" ChemBiochem 2003, 4, pp. 1129-1136.
Banerjea Akhil et al., "Inhibition of HIV-1 by lentiviral vector-transduced siRNAs in T lymphocytes differentiated in SCID-hu mice and CD34+ progenitor cell-derived macrophages", Molecular Therapy : The Journal of American Society of Gene Therapy, Jul. 2003, pp. 62-71, vol. 8, No. 1.
Barton G M et al., "Retroviral delivery of small interfering RNA into primary cells", Proceeding of the National Academy of Sciences of USA, Nov. 12, 2002, pp. 14943-14945, vol. 99, No. 23, Washington, USA.
Bjorklund et al., "Embryonic stem cells develop into functional dopaminergic neurons after transplantation in a Parkinson rat model," Proc. Natl. Acad. Sci., vol. 99, No. 4, pp. 2344-2349, 2002.
Branch, Trends in Biochem. Sci., "A good antisense molecule is hard to find," vol. 23, pp. 45-50, 1998.
Brummelkamp T R et al., "A System for Stable Expression of Short Interfering RNAs in Mammalian Cells," Science, Apr. 19, 2002, vol. 296.
Caplen, N J et al., "Specific inhibition of gene expression by small double-stranded RNAs in invertebrate and vertebrate systems," PNAS, Aug. 14, 2001, vol. 98, No. 17.
Chirila et al., "The use of synthetic polymers for delivery of therapeutic antisense oligodeoxynucleotides," Biomaterials, vol. 23, pp. 321-342, 2002.
Consiglio et al., "In vivo gene therapy of metachromatic leukodystrophy by lentiviral vectors: correction of neuropathology and protection against learning impairments in affected mice", Nature Medicine, Mar. 2001, pp. 310-316, vol. 7, No. 3.
Crooke, Antisense Res. and Application, pp. 1-50 Ed. By S. Crooker, Springer-Verlat, Publ., 1998.

(Continued)

Primary Examiner — Jane Zara
(74) Attorney, Agent, or Firm — Knobbe, Martens, Olson & Bear LLP

(57) ABSTRACT

The invention provides methods and compositions for the expression of small RNA molecules within a cell using a lentiviral vector. The methods can be used to express doubles stranded RNA complexes. Small interfering RNA (siRNA) can be expressed using the methods of the invention within a cell, which are capable of down regulating the expression of a target gene through RNA interference. A variety of cells can be treated according to the methods of the invention including embryos, embryogenic stem cells, allowing for the generation of transgenic animals or animals constituted partly by the transduced cells that have a specific gene or a group of genes down regulated.

14 Claims, 7 Drawing Sheets

OTHER PUBLICATIONS

Czauderna Frank et al., "Inducible shRNA expression for application in a prostate cancer mouse model", Nucleic Acids Research, Nov. 1, 2003, p. e127, vol. 31, No. 21.

De Palma et al., "In Vivo Targeting of Tumor Endothelial Cells by Systemic Delivery of Lentiviral Vectors", Human Gene Therapy, Aug. 10, 2003, pp. 1193-1206, vol. 14.

Devroe E. & Silver P A, "Retrovirus-delivered siRNA", BMC Technology, Aug. 28, 2002, pp. 1-5.

Gatlin et al., "Long-term engraftment of nonobese diabetic/severe combined immunodeficient mice with human CD34+ cells tranduced by a self-inactivating human immunodeficiency virus type I vector," Human Gene Therapy, vol. 12, pp. 1079-1089, Jun. 2001.

Sui G et al., "A DNA vector-based RNAi technology to suppress gene expression in mammalian cells," PNAS, Apr. 16, 2002, vol. 99, No. 8.

Timmons et al., "Specific interference by ingested dsRNA," Nature, vol. 395, p. 854, Oct. 1998.

University of Pennsylvania Health System, "Mutant Gene Products Strong Natural Resistant to HIV-1 Infection in 1 in 100 People" Aug. 8, 1996.

Van De Wetering Marc et al., "Specific inhibition of gene expression using a stably integrated, inducible small-interfering-RNA vector", EMBO Reports, Jun. 2003, pp. 609-615, vol. 4, No. 6.

Yang Shi, "Mammalian RNAi for the masses," Trends in Genetics, vol. 19, No. 1, Jan. 2003, pp. 9-12.

Yu Jenn-Yah et al., "RNA interference by expression of short-interfering RNAs and hairpin RNAs in mammalian cells", Proceeding of the National Academy of Sciences of USA, Apr. 30, 1002, pp. 6047-6052, vol. 99, No. 9, Washington, USA, 2002.

Zennou V et al. "HIV-1 Genome Nuclear Import is Mediated by a Central DNA Flap," Cell, Apr. 14, 2000, vol. 101, 173-185.

Zufferey R. et al., "Woodchuck hepatitis virus posttranscriptional regulatory element enhances expression of transgenes delivered by retroviral vectors", Journal of Virology, 1999, pp. 2886-2892, vol. 74, No. 4.

Godwin et al., "Detection of targeted GFP-Hox gene fusion during mouse embryogenesis," PNAS, vol. 95, pp. 10342-10347, 1998.

Hemmati-Vrivanlou et al., "Vertebrate Embryonic Cells Will Become Nerve Cells Unless Told Otherwise," Cell, vol. 88, pp. 13-17, 1997.

Howard Hughes Medical Institute, "Pushing the Envelope" Nov. 21, 1997.

Ilves et al., "Retroviral vectors designed for targeted expression of RNA polymerase III-driven transcripts: a comparative study," Gene, 171 (1996) 203-208.

Iwakuma et al. "self-inactivating lentiviral vectors with U3 and U5 modifications," Virology, vol. 261, 120-132, 1999.

Jacque J-M et al., "Modulation of HIV-1 Replication by RNA Interference," Nature, Jul. 25, 2002, vol. 418.

Junker et al., "Reduction in replication of the human immunodeficiency virus type I in human T cell lines by polymerase III-driven transcription of chemeric tRNA-antisense RNA genes," Antisense Research and Development, vol. 4, pp. 165-172, 1994.

Kafri et al, "Lentiviral vectors: regulated gene expression," Molecular Therapy, vol. 1, No. 6, pp. 516-521, Jun. 2000.

Kawasaki et al., "Induction of Midbrain Dopaminergic Neurons from ES Cells by Stromal Cell—Derived Inducing Activity," Neuron, vol. 28, pp. 31-40, 2000.

Lawrence D., "RNAi could hold promise in the treatment of HIV," the Lancet, Jun. 8, 2002, vol. 359.

Lee N S et al., "Expression of small interfering RNAs targeted against HIV-1 rev transcripts in human cells", Nature Biotechnology, May 2002, pp. 500-505, vol. 19.

Li et al., "Inhibition of HIV-1 infection by lentiviral vectors expressing pol III-promoted anti-HIV RNAs", Molecular Therapy, Academic Press, Aug. 2003, pp. 196-206, vol. 8, No. 2, San Diego, CA, USA.

Lieberman et al., "Interfering with disease: opportunities and roadblocks to harnessing RNA interference," Trends in Molecular Medicine, vol. 9, No. 9, Sep. 2003, pp. 397-403.

Lois Carlos et al., "Germline transmission and tissue-specific expression of transgenes delivered by lentiviral vectors", Science, Feb. 1, 2002, pp. 868-872, vol. 295, No. 5556.

Martinez L J, "Katy, bar the door! HIV entry inhibitors," Research Initiative/Treatment Action!, Jun. 2000.

Matsukura S et al., "Establishment of conditional vectors for hairpin siRNA knockdowns", Nucleic Acids Research, Aug. 1, 2003, pp. e77-1, vol. 31, No. 15, Oxford University.

Michienzi et al., "RNA-Mediated Inhibition of HIV in a Gene Therapy Setting," Ann. N.Y. Acad. Sci., 1002:63-71 (2003).

Miyagishi M. et al., "U6 promoter-driven sirnas with four uridine 3" overhangs efficiently suppress targeted gene expression in mammalian cells", Nature Biotechnology, May 2002, pp. 497-500, vol. 19, No. 5, US.

Miyoshi et al., "Stable and efficient gene transfer into the retina using an HIV-based lentiviral vector", Proc. Natl. Acad. Sci. USA, Sep. 1997, pp. 10319-10323, vol. 94.

Miyoshi H. et al. "Development of a self-inactivating lentivirus vector", Journal of Virology, 1998, pp. 8150-8157, vol. 72, No. 10.

Naldini L. et al. "In Vivo Gene Delivery and Stable Transduction of Nondividing Cells by a Lentiviral Vector," Science, Apr. 12, 1996, vol. 272.

National Cancer Institute, "Scientists suggest new approaches for development of AIDS Drugs and Vaccines," Charity Wire, Jun. 21, 1999.

Novina C. D. et al.,, "siRNA-directed inhibition of HIV-1 infection," Nature Medicine, Jul. 2002, vol. 8, No. 7.

Odorico et al., "Multilineage differentiation from human embryonic stem cell lines," Stem Cells, vol. 19, pp. 193-204, 2001.

Ogueta et al., "Design and in vitro characterization of a single regulatory module for efficient control of gene expression in both plasmid DNA and a self-inactivating lentiviral vector," Molecular Medicine, vol. 7, No. 8, pp. 569-579, 2001.

Ohkawa J. et al., " Control of the functional activity of an antisense RNA by a tetracycline-responsive derivative of the human U6 snRNA promoter", Human Gene Therapy, Mar. 1, 2000, pp. 577-585, vol. 11, No. 4.

Paddison P J et al., "Short hairpin RNAs (shRNAs) induce sequence-specific silencing in mammalian cells," Genes & Development, Mar. 8, 2002, 16:948-958.

Paul C P et al., "Effective expression of small interfering RNA in human cells", Nature Biotechnology, May 2002, vol. 20, No. 5, US.

Peracchi et al. "Prospects for antiviral ribozymes and deoxyribozymes," Rev. Med. Virol, vol. 14, pp. 47-64, 2004.

Pomerantz, "RNA interference meets HIV-1: Will silence be golden?", Nature Medicine, vol. 8, p. 659-660, Jul. 2002.

Qin X-F et al., "Inhibiting HIV-1 infection in human T cells by lentiviral-mediated delivery of small interfering RNA against CCR5", Proceeding of the National Academy of Sciences of USA, Jan. 7, 2003, pp. 183-188, vol. 100, No. 1, Washington, USA.

Reiser et al. "Development of multigene and regulated lentivirus vectors," J. Virol., vol. 74, No. 22, pp. 10589-10599, Nov. 2000.

Rubinson et al., "A lentivirus-based system to functionally silence genes in primary mammalian cells, stem cells, and transgenic mice by RNA interference," Nature Genetics, vol. 33, pp. 401-407 (Mar. 2003).

Shankar P. "RNAi-Mediated Inhibition of HIV-1 Replication in Primary Macrophages," Center for Blood Research, Boston, 2003.

Sirven A. et al., "The human immunodeficiency virus type-1 central DNA flap is a crucial determinant for lentiviral vector nuclear import and gene transduction of human hematopoietic stem cells", W.B. Saunders Company, Dec. 15, 2000, pp. 4103-4110, vol. 96, No. 13, Orlando, Florida.

An et al., Stable reduction of CCR5 by RNAi through hematopoietic stem cell transplant in non-human primates, PNAS, 104(32): 13110-13115, 2007.

* cited by examiner

SEQUENCE LISTING

<160> NUMBER OF SEQ ID NOS: 5

<210> SEQ ID NO 1
<211> LENGTH: 59
<212> TYPE: DNA
<213> ORGANISM: Artificial Sequence
<220> FEATURE:

<223> OTHER INFORMATION: This represents a siRNA cassette comprising
      bacterial sequence and synthetic linker, loop and
      terminator sequences.

<400> SEQUENCE: 1
gatccccgtg accagcgaat acctgtttca agagaacagg tattcgctgg tcactttttt    59

<210> SEQ ID NO 2
<211> LENGTH: 9941
<212> TYPE: DNA
<213> ORGANISM: Artificial Sequence
<220> FEATURE:
<223> OTHER INFORMATION: This sequence represents a lentiviral vector
      comprising a human immunodeficiency virus flap
      sequence, a green fluorescent protein variant
      sequence, a human ubiquitin promoter sequence and
      a woodchuck hepatitis regulator element sequence.

<400> SEQUENCE: 2
gtcgacggat cgggagatct cccgatcccc tatggtgcac tctcagtaca atctgctctg      60
atgccgcata gttaagccag tatctgctcc ctgcttgtgt gttggaggtc gctgagtagt     120
gcgcgagcaa aatttaagct acaacaaggc aaggcttgac cgacaattgc atgaagaatc     180
tgcttagggt taggcgtttt gcgctgcttc gcgatgtacg ggccagatat acgcgttgac     240
attgattatt gactagttat taatagtaat caattacggg gtcattagtt catagcccat     300
atatggagtt ccgcgttaca taacttacgg taaatggccc gcctggctga ccgcccaacg     360
acccccgccc attgacgtca ataatgacgt atgttcccat agtaacgcca atagggactt     420
tccattgacg tcaatgggtg gagtatttac ggtaaactgc ccacttggca gtacatcaag     480
tgtatcatat gccaagtacg ccccctattg acgtcaatga cggtaaatgg cccgcctggc     540
attatgccca gtacatgacc ttatgggact ttcctacttg gcagtacatc tacgtattag     600
tcatcgctat taccatggtg atgcggtttt ggcagtacat caatgggcgt ggatagcggt     660
ttgactcacg gggatttcca agtctccacc ccattgacgt caatgggagt ttgttttggc     720
accaaaatca acgggacttt ccaaaatgtc gtaacaactc cgccccattg acgcaaatgg     780
gcggtaggcg tgtacggtgg gaggtctata taagcagcgc gttttgcctg tactgggtct     840
ctctggttag accagatctg agcctgggag ctctctggct aactagggaa cccactgctt     900
aagcctcaat aaagcttgcc ttgagtgctt caagtagtgt gtgcccgtct gttgtgtgac     960
tctggtaact agagatccct cagacccttt tagtcagtgt ggaaaatctc tagcagtggc    1020
gcccgaacag ggacttgaaa gcgaaaggga accagagga gctctctcga cgcaggactc     1080
ggcttgctga agcgcgcacg gcaagaggcg aggggcggcg actggtgagt acgccaaaaa    1140
ttttgactag cggaggctag aaggagagag atggtgcga gagcgtcagt attaagcggg     1200
ggagaattag atcgcgatgg gaaaaaattc ggttaaggcc agggggaaag aaaaaatata    1260
aattaaaaca tatagtatgg gcaagcaggg agctagaacg attcgcagtt aatcctggcc    1320
tgttagaaac atcagaaggc tgtagacaaa tactgggaca gctacaacca tcccttcaga    1380
caggatcaga agaacttaga tcattatata atacagtagc aaccctctat tgtgtgcatc    1440
aaaggataga gataaaagac accaaggaag ctttagacaa gatagaggaa gagcaaaaca    1500
aaagtaagac caccgcacag caagcggccg ctgatcttca gacctggagg aggagatatg    1560
agggacaatt ggagaagtga attatataaa tataaagtag taaaaattga accattagga    1620
gtagcaccca ccaaggcaaa gagaagagtg gtgcagagag aaaaaagagc agtgggaata    1680
ggagctttgt tccttgggtt cttgggagca gcaggaagca ctatgggcgc agcgtcaatg    1740

```
acgctgacgg tacaggccag acaattattg tctggtatag tgcagcagca gaacaatttg   1800
ctgagggcta ttgaggcgca acagcatctg ttgcaactca cagtctgggg catcaagcag   1860
ctccaggcaa gaatcctggc tgtggaaaga tacctaaagg atcaacagct cctgggatt    1920 tggggttgct ctggaaaact catttgcacc actgctgtgc cttggaatgc tagttggagt   1980
aataaatctc tggaacagat ttggaatcac acgacctgga tggagtggga cagagaaatt   2040
aacaattaca caagcttaat acactcctta attgaagaat cgcaaaacca gcaagaaaag   2100
aatgaacaag aattattgga attagataaa tgggcaagtt tgtggaattg gtttaacata   2160
acaaattggc tgtggtatat aaaattattc ataatgatag taggaggctt ggtaggttta   2220
agaatagttt ttgctgtact ttctatagtg aatagagtta ggcagggata ttcaccatta   2280
tcgtttcaga cccacctccc aaccccgagg ggacccgaca ggcccgaagg aatagaagaa   2340
gaaggtggag agagagacag agacagatcc attcgattag tgaacggatc ggcactgcgt   2400
gcgccaattc tgcagacaaa tggcagtatt catccacaat tttaaaagaa aaggggggat   2460
tggggggtac agtgcagggg aaagaatagt agacataata gcaacagaca tacaaactaa   2520
agaattacaa aaacaaatta caaaaattca aaattttcgg gtttattaca gggacagcag   2580
agatccagtt tggttaatta agggtgcagc ggcctccgcg ccgggttttg gcgcctcccg   2640
cgggcgcccc cctcctcacg gcgagcgctg ccacgtcaga cgaagggcgc aggagcgttc   2700
ctgatccttc cgcccggacg ctcaggacag cggcccgctg ctcataagac tcggccttag   2760
aaccccagta tcagcagaag gacattttag gacgggactt gggtgactct agggcactgg   2820 ttttcttttcc agagagcgga acaggcgagg aaaagtagtc ccttctcggc gattctgcgg   2880
agggatctcc gtggggcggt gaacgccgat gattatataa ggacgcgccg ggtgtggcac   2940
agctagttcc gtcgcagccg ggatttgggt cgcggttctt gtttgtggat cgctgtgatc   3000
gtcacttggt gagttgcggg ctgctgggct ggccggggct ttcgtggccg ccgggccgct   3060
cggtgggacg gaagcgtgtg gagagaccgc caagggctgt agtctgggtc cgcgagcaag   3120
gttgccctga actgggggtt ggggggagcg cacaaaatgg cggctgttcc cgagtcttga   3180
atggaagacg cttgtaaggc gggctgtgag gtcgttgaaa caaggtgggg ggcatggtgg   3240
gcggcaagaa cccaaggtct tgaggccttc gctaatgcgg gaaagctctt attcgggtga   3300
gatgggctgg ggcaccatct ggggaccctg acgtgaagtt tgtcactgac tggagaactc   3360
gggtttgtcg tctggttgcg ggggcggcag ttatgcggtg ccgttgggca gtgcacccgt   3420
acctttggga gcgcgcgcct cgtcgtgtcg tgacgtcacc cgttctgttg gcttataatg   3480
cagggtgggg ccacctgccg gtaggtgtgc ggtaggcttt tctccgtcgc aggacgcagg   3540
gttcgggcct agggtaggct ctcctgaatc gacaggcgcc ggacctctgg tgaggggagg   3600
gataagtgag gcgtcagttt ctttggtcgg ttttatgtac ctatcttctt aagtagctga   3660
agctccggtt ttgaactatg cgctcggggt tggcgagtgt gttttgtgaa gttttttagg   3720 cacctttga aatgtaatca tttgggtcaa tatgtaattt tcagtgttag actagtaaag   3780
cttctgcagg tcgactctag aaaattgtcc gctaaattct ggccgttttt ggcttttttg   3840
ttagacagga tccccgggta ccggtcgcca ccatggtgag caagggcgag gagctgttca   3900
ccggggtggt gcccatcctg gtcgagctgg acggcgacgt aaacggccac aagttcagcg   3960
tgtccggcga gggcgagggc gatgccacct acggcaagct gaccctgaag ttcatctgca   4020
ccaccggcaa gctgcccgtg ccctggccca cctcgtgac cacccctgacc tacggcgtgc   4080 agtgcttcag ccgctacccc gaccacatga agcagcacga cttcttcaag tccgccatgc   4140
```

```
ccgaaggcta cgtccaggag cgcaccatct tcttcaagga cgacggcaac tacaagaccc   4200
gcgccgaggt gaagttcgag gcgacaccc tggtgaaccg catcgagctg aagggcatcg    4260
acttcaagga ggacggcaac atcctggggc acaagctgga gtacaactac aacagccaca   4320
acgtctatat catggccgac aagcagaaga acggcatcaa ggtgaacttc aagatccgcc   4380
acaacatcga ggacggcagc gtgcagctcg ccgaccacta ccagcagaac ccccccatcg   4440
gcgacggccc cgtgctgctg cccgacaacc actacctgag cacccagtcc gccctgagca   4500
aagaccccaa cgagaagcgc gatcacatgg tcctgctgga gttcgtgacc gccgccggga   4560
tcactctcgg catggacgag ctgtacaagt aaagcggccg cgactctaga attcgatatc   4620
aagcttatcg ataatcaacc tctggattac aaaatttgtg aaagattgac tggtattctt   4680
aactatgttg ctccttttac gctatgtgga tacgctgctt taatgccttt gtatcatgct   4740
attgcttccc gtatggcttt catttctcc tccttgtata aatcctggtt gctgtctctt   4800
tatgaggagt tgtggcccgt tgtcaggcaa cgtggcgtgg tgtgcactgt gtttgctgac   4860
gcaaccccca ctggttgggg cattgccacc acctgtcagc tcctttccgg gactttcgct   4920 ttcccctcc ctattgccac ggcggaactc atcgccgcct gccttgcccg ctgctggaca   4980
ggggctcggc tgttgggcac tgacaattcc gtggtgttgt cggggaaatc atcgtccttt   5040
ccttggctgc tcgcctgtgt tgccacctgg attctgcgcg gacgtccctt ctgctacgtc   5100
ccttcggccc tcaatccagc ggaccttcct tcccgcggcc tgctgccggc tctgcggcct   5160
cttccgcgtc ttcgccttcg ccctcagacg agtcggatct ccctttggcc cgcctccccg   5220
catcgatacc gtcgacctcg agacctagaa aaacatggag caatcacaag tagcaataca   5280
gcagctacca atgctgattg tgcctggcta aagcacaag aggaggagga ggtgggtttt   5340
ccagtcacac ctcaggtacc tttaagacca atgacttaca aggcagctgt agatcttagc   5400
cactttttaa agaaaaggg gggactgaa gggctaattc actcccaacg aagacaagat   5460
atccttgatc tgtggatcta ccacacacaa ggctacttcc ctgattggca gaactacaca   5520
ccagggccag ggatcagata tccactgacc tttggatggt gctacaagct agtaccagtt   5580
gagcaagaga aggtagaaga agccaatgaa ggagagaaca cccgcttgtt acaccctgtg   5640
agcctgcatg ggatggatga cccggagaga gaagtattag agtggaggtt tgacagccgc   5700
ctagcatttc atcacatggc ccgagagctg catccggact gtactgggtc tctctggtta   5760
gaccagatct gagcctggga gctctctggc taactaggga acccactgct taagcctcaa   5820
taaagcttgc cttgagtgct tcaagtagtg tgtgcccgtc tgttgtgtga ctctggtaac   5880
tagagatccc tcagaccctt ttagtcagtg tggaaaatct ctagcagggc cgtttaaac   5940 ccgctgatca gcctcgactg tgccttctag ttgccagcca tctgttgttt gcccctcccc   6000
cgtgccttcc ttgaccctgg aaggtgccac tcccactgtc ctttcctaat aaaatgagga   6060
aattgcatcg cattgtctga gtaggtgtca ttctattctg gggggtgggg tgggcagga    6120 cagcaagggg gaggattggg aagacaatag caggcatgct ggggatgcgg tgggctctat   6180
ggcttctgag gcgaaagaa ccagctgggg ctctaggggg tatccccacg cgccctgtag   6240
cggcgcatta agcgcggcgg gtgtggtggt tacgcgcagc gtgaccgcta cacttgccag   6300
cgccctagcg cccgctcctt tcgctttctt cccttccttt ctcgccacgt tcgccggctt   6360
tccccgtcaa gctctaaatc gggggctccc tttagggttc cgatttagtg ctttacggca   6420
cctcgacccc aaaaaacttg attagggtga tggttcacgt agtgggccat cgccctgata   6480
gacggttttt cgccctttga cgttggagtc cacgttcttt aatagtggac tcttgttcca   6540
```

```
aactggaaca acactcaacc ctatctcggt ctattctttt gatttataag ggattttgcc    6600
gatttcggcc tattggttaa aaaatgagct gatttaacaa aaatttaacg cgaattaatt    6660
ctgtggaatg tgtgtcagtt agggtgtgga aagtccccag gctccccagc aggcagaagt    6720
atgcaaagca tgcatctcaa ttagtcagca accaggtgtg gaaagtcccc aggctcccca    6780
gcaggcagaa gtatgcaaag catgcatctc aattagtcag caaccatagt cccgccccta    6840
actccgccca tcccgcccct aactccgccc agttccgccc attctccgcc ccatggctga    6900
ctaattttt ttatttatgc agaggccgag gccgcctctg cctctgagct attccagaag    6960
tagtgaggag gcttttttgg aggcctaggc ttttgcaaaa agctcccggg agcttgtata    7020
tccattttcg gatctgatca gcacgtgttg acaattaatc atcggcatag tatatcggca    7080
tagtataata cgacaaggtg aggaactaaa ccatggccaa gttgaccagt gccgttccgg    7140
tgctcaccgc gcgcgacgtc gccggagcgg tcgagttctg gaccgaccgg ctcgggttct    7200
cccgggactt cgtggaggac gacttcgccg gtgtggtccg ggacgacgtg accctgttca    7260
tcagcgcggt ccaggaccag gtggtgccgg acaacaccct ggcctgggtg tgggtgcgcg    7320
gcctggacga gctgtacgcc gagtggtcgg aggtcgtgtc cacgaacttc cgggacgcct    7380
ccgggccggc catgaccgag atcggcgagc agccgtgggg gcgggagttc gccctgcgcg    7440
acccggccgg caactgcgtg cacttcgtgg ccgaggagca ggactgacac gtgctacgag    7500
atttcgattc caccgccgcc ttctatgaaa ggttgggctt cggaatcgtt ttccgggacg    7560
ccggctggat gatcctccag cgcggggatc tcatgctgga gttcttcgcc cacccccaact   7620
tgtttattgc agcttataat ggttacaaat aaagcaatag catcacaaat ttcacaaata    7680
aagcattttt ttcactgcat tctagttgtg gtttgtccaa actcatcaat gtatcttatc    7740
atgtctgtat accgtcgacc tctagctaga gcttggcgta atcatggtca tagctgtttc    7800
ctgtgtgaaa ttgttatccg ctcacaattc cacacaacat acgagccgga agcataaagt    7860
gtaaagcctg gggtgcctaa tgagtgagct aactcacatt aattgcgttg cgctcactgc    7920
ccgctttcca gtcgggaaac ctgtcgtgcc agctgcatta atgaatcggc caacgcgcgg    7980
ggagaggcgg tttgcgtatt gggcgctctt ccgcttcctc gctcactgac tcgctgcgct    8040
cggtcgttcg gctgcggcga gcggtatcag ctcactcaaa ggcggtaata cggttatcca    8100
cagaatcagg ggataacgca ggaaagaaca tgtgagcaaa aggccagcaa aaggccagga    8160
accgtaaaaa ggccgcgttg ctggcgtttt tccataggct ccgcccccct gacgagcatc    8220
acaaaaatcg acgctcaagt cagaggtggc gaaacccgac aggactataa agataccagg    8280
cgtttccccc tggaagctcc ctcgtgcgct ctcctgttcc gaccctgccg cttaccggat    8340
acctgtccgc ctttctccct tcgggaagcg tggcgctttc tcatagctca cgctgtaggt    8400
atctcagttc ggtgtaggtc gttcgctcca agctgggctg tgtgcacgaa ccccccgttc    8460
agcccgaccg ctgcgcctta tccggtaact atcgtcttga gtccaacccg gtaagacacg    8520
acttatcgcc actggcagca gccactggta acaggattag cagagcgagg tatgtaggcg    8580
gtgctacaga gttcttgaag tggtggccta actacggcta cactagaaga acagtatttg    8640
gtatctgcgc tctgctgaag ccagttacct tcggaaaaag agttggtagc tcttgatccg    8700
gcaaacaaac caccgctggt agcggtggtt ttttgtttg caagcagcag attacgcgca    8760
gaaaaaaagg atctcaagaa gatcctttga tcttttctac ggggtctgac gctcagtgga    8820
acgaaaactc acgttaaggg attttggtca tgagattatc aaaaaggatc ttcacctaga    8880
tccttttaaa ttaaaaatga agttttaaat caatctaaag tatatatgag taaacttggt    8940
```

```
ctgacagtta ccaatgctta atcagtgagg cacctatctc agcgatctgt ctatttcgtt    9000
catccatagt tgcctgactc cccgtcgtgt agataactac gatacgggag ggcttaccat    9060
ctggccccag tgctgcaatg ataccgcgag acccacgctc accggctcca gatttatcag    9120
caataaacca gccagccgga agggccgagc gcagaagtgg tcctgcaact ttatccgcct    9180
ccatccagtc tattaattgt tgccgggaag ctagagtaag tagttcgcca gttaatagtt    9240
tgcgcaacgt tgttgccatt gctacaggca tcgtggtgtc acgctcgtcg tttggtatgg    9300
cttcattcag ctccggttcc caacgatcaa ggcgagttac atgatccccc atgttgtgca    9360
aaaaagcggt tagctccttc ggtcctccga tcgttgtcag aagtaagttg gccgcagtgt    9420
tatcactcat ggttatggca gcactgcata attctcttac tgtcatgcca tccgtaagat    9480
gcttttctgt gactggtgag tactcaacca agtcattctg agaatagtgt atgcggcgac    9540
cgagttgctc ttgcccggcg tcaatacggg ataataccgc gccacatagc agaactttaa    9600
aagtgctcat cattggaaaa cgttcttcgg ggcgaaaact ctcaaggatc ttaccgctgt    9660
tgagatccag ttcgatgtaa cccactcgtg cacccaactg atcttcagca tcttttactt    9720
tcaccagcgt ttctgggtga gcaaaaacag gaaggcaaaa tgccgcaaaa aagggaataa    9780
gggcgacacg gaaatgttga atactcatac tcttcctttt tcaatattat tgaagcattt    9840
atcagggtta ttgtctcatg agcggataca tatttgaatg tatttagaaa aataaacaaa    9900 tagggggttcc gcgcacattt ccccgaaaag tgccacctga c                       9941

<210> SEQ ID NO 3
<211> LENGTH: 233
<212> TYPE: DNA
<213> ORGANISM: Homo sapiens

<400> SEQUENCE: 3
gaattcgaac gctgacgtca tcaacccgct ccaaggaatc gcgggcccag tgtcactagg     60
cgggaacacc cagcgcgcgt gcgccctggc aggaagatgg ctgtgaggga caggggagtg    120
gcgccctgca atatttgcat gtcgctatgt gttctgggaa atcaccataa acgtgaaatg    180
tctttggatt tgggaatctt ataagttctg tatgagacca cagatctaag ctt           233

<210> SEQ ID NO 4
<211> LENGTH: 355
<212> TYPE: DNA
<213> ORGANISM: Artificial Sequence
<220> FEATURE:
<223> OTHER INFORMATION: This represents a mutant human sequence having
      an introduced bacterial tetO1 binding site.

<400> SEQUENCE: 4
gggaattccc ccagtggaaa gacgcgcagg caaaacgcac cacgtgacgg agcgtgaccg     60
cgcgccgagc ccaaggtcgg gcaggaagag ggcctatttc ccatgattcc ttcatatttg    120
catatacgat acaaggctgt tagagagata attagaatta atttgactgt aaacacaaag    180
atattagtac aaaatacgtg acgtagaaag taataaattc ttgggtagtt tgcagtttta    240
aaattatgtt ttaaaatgga ctatcatatg cttaccgtaa cttgaaagta ctctatcatt    300
gatagagtta tatatcttgt ggaaaggacg aaacaccgtg gtcttcaagc ttccg         355

<210> SEQ ID NO 5
<211> LENGTH: 634
<212> TYPE: DNA
<213> ORGANISM: E. coli

<400> SEQUENCE: 5
```

```
gctagccacc atgtccagat tagataaaag taaagtgatt aacagcgcat tagagctgct      60
taatgaggtc ggaatcgaag gtttaacaac ccgtaaactc gcccagaagc taggtgtaga     120
gcagcctaca ttgtattggc atgtaaaaaa taagcgggct ttgctcgacg ccttagccat     180
tgagatgtta gataggcacc atactcactt ttgcccttta gaaggggaaa gctggcaaga     240 tttttacgt aataacgcta aaagttttag atgtgcttta ctaagtcatc gcgatggagc      300
aaaagtacat ttaggtacac ggcctacaga aaaacagtat gaaactctcg aaaatcaatt     360 agcctttta tgccaacaag gtttttcact agagaatgca ttatatgcac tcagcgctgt     420
ggggcatttt actttaggtt gcgtattgga agatcaagag catcaagtcg ctaaagaaga     480
aagggaaaca cctactactg atagtatgcc gccattatta cgacaagcta tcgaattatt     540
tgatcaccaa ggtgcagagc cagccttctt attcggcctt gaattgatca tatgcggatt     600
agaaaaacaa cttaaatgtg aaagtgggtc ttaa                                 634
```

METHOD FOR EXPRESSION OF SMALL RNA MOLECULES WITHIN A CELL

REFERENCE TO RELATED APPLICATIONS

The present application is a continuation of U.S. patent application Ser. No. 10/243,816, filed Sep. 13, 2002, which claims priority under 35 U.S.C. §119(e) to U.S. Provisional Application No. 60/322,031, filed Sep. 13, 2001, U.S. Provisional Application No. 60/347,782, filed Jan. 9, 2002, U.S. Provisional Application No. 60/389,592, filed Jun. 18, 2002, and U.S. Provisional Application No. 60/406,436, filed Aug. 27, 2002. All of the aforementioned priority applications are hereby incorporated by reference in their entireties.

GOVERNMENT SUPPORT

This invention was made with government support under Grant Number GM39458 awarded by the National Institutes of Health. The United States Government has certain rights in the invention.

BACKGROUND OF THE INVENTION

1. Field of the Invention

The present invention relates generally to methods for altering gene expression in a cell or an animal using viral constructs engineered to deliver an RNA molecule. In a more specific aspect, a viral construct is used to deliver double-stranded RNA molecules that can be used to down-regulate or modulate gene expression.

2. Description of the Related Art

RNA interference (RNAi) or silencing is a recently discovered phenomenon (A. Fire et al., *Nature* 391, 806 (1998); C. E. Rocheleau et al. *Cell* 90, 707 (1997)). Small interfering RNAs ("siRNAs") are double-stranded RNA molecules that inhibit the expression of a gene with which they share homology. siRNAs have been used as a tool to down regulate the expression of specific genes in a variety of cultured cells as well as in invertebrate animals. A number of such approaches have been reviewed recently (P. D. Zamore *Science* 296, 1265 (2002)); however, such approaches have limitations. For example, no technique prior to the invention described herein allows for the generation of transgenic mammal having a specific gene down regulated through RNA interference. Similarly, there is a need for more robust methods for the introduction of small RNA molecules with regulatory function. The invention provided herein addresses these and other limitations in the field of RNA mediated gene regulation.

SUMMARY OF THE INVENTION

The invention relates generally to methods to express within a cell an RNA molecule or molecules. These methods can be used with a wide variety of cell types. RNA molecules can be expressed within a cell for a variety of purposes. For example, and without limitation, RNA molecules can serve as markers within a cell, can act as antisense oligonucleotides or ribozymes for regulating gene expression, and can serve to down regulate genes through RNA interference.

In one aspect, the invention provides retroviral constructs for the expression of an RNA molecule or molecules within a cell. The constructs preferably comprise a nucleic acid having the R and U5 sequences from a 5' lentiviral long terminal repeat (LTR), a self-inactivating lentiviral 3' LTR, and a RNA Polymerase III (pol III) promoter. The retroviral constructs preferably comprise an RNA coding region operably linked to the RNA Polymerase III promoter. The RNA coding region preferably comprises a DNA sequence that can serve as a template for the expression, of a desired RNA molecule.

The RNA coding region can be immediately followed by a pol III terminator sequence which directs the accurate and efficient termination of RNA synthesis by pol III. The pol III terminator sequences generally comprise 4 or more consecutive T residues. In a preferred embodiment, a cluster of 5 consecutive Ts is used as the terminator by which pol III transcription is stopped at second or third T of the DNA template. As a result, only 2 to 3 U residues are added to the 3' end of the RNA that is synthesized from the RNA coding region.

A variety of pol III promoters can be used with the invention, including for example, the promoter fragments derived from H1 RNA genes or U6 sn RNA genes of human or mouse origin or from any other species. In addition, pol III promoters can be modified/engineered to incorporate other desirable properties such as to be inducible by small chemical molecules either ubiquitously or in a tissue-specific manner, for example, one activated with tetracycline or IPTG (lacI system).

The pol III promoter, RNA template region and pol III terminator together may comprise an "RNA cassette" or "RNA expression cassette." If the RNA is a small inhibitory RNA (siRNA), the expression cassette may be termed an "siRNA expression cassette."

In one embodiment, the RNA coding region encodes a self-complementary RNA molecule having a sense region, an antisense region and a loop region. Such an RNA molecule when expressed desirably forms a "hairpin" structure. The loop region is generally between about 2 and about 10 nucleotides in length. In a preferred embodiment, the loop region is from about 6 and about 9 nucleotides in length. In one such embodiment of the invention, the sense region and the antisense region are between about 15 and about 30 nucleotides in length.

In one embodiment, the RNA coding region is operably linked downstream to an RNA Polymerase III promoter such that the RNA coding sequence can be precisely expressed without any extra non-coding nucleotides present at 5' end. In this way an RNA sequence can be expressed that is identical to a target sequence at the 5' end. The synthesis of the RNA coding region is ended at the terminator site. In one preferred embodiment the terminator consists of five consecutive T residues.

In another aspect of the invention, the retroviral vector can comprise multiple RNA coding regions. In one embodiment, the retroviral construct comprises a first RNA pol III promoter, a first coding region encoding a first RNA molecule operably linked to the first RNA pol III promoter, a second RNA pol III promoter and a second RNA coding region operably linked to the second RNA pol III promoter. Preferably, the second RNA coding region encodes an RNA molecule that is substantially complementary to the RNA molecule encoded by the first RNA coding region, such that the two RNA molecules can form a double-stranded structure when expressed. The methods of invention also include multiple RNA coding regions that encode hairpin-like self-complementary RNA molecules or other non-hairpin molecules.

In yet another embodiment of the invention, the retroviral construct comprises a first RNA pol III promoter operably linked to a first RNA coding region, and a second RNA pol III promoter operably linked to the same first RNA coding region in the opposite direction, such that expression of the RNA coding region from the first RNA pol III promoter results in a synthesis of a first RNA molecule as the sense strand and expression of the RNA coding region from the second RNA pol III promoter results in synthesis of a second RNA molecule as an antisense strand that is substantially complementary to the first RNA molecule. In one such embodiment, both RNA Polymerase III promoters are separated from the RNA coding region by termination sequences, preferably termination sequences having five consecutive T residues.

According to one embodiment of the invention, the 5' LTR sequences in the retroviral construct are derived from HIV. The retroviral construct may also comprise a woodchuck hepatitis virus enhancer element sequence and/or a tRNA amber suppressor sequence.

In another embodiment of the invention, the self-inactivating 3' LTR is a U3 element with a deletion of its enhancer sequence. In yet another embodiment, the self-inactivating 3' LTR is a modified HIV 3' LTR.

The recombinant retroviral construct can be pseudotyped, for example with the vesicular stomatitits virus envelope glycoprotein.

In another aspect of the invention, expression of the RNA coding region results in the down regulation of a target gene. Preferably the target gene comprises a sequence that is at least about 90% identical with the RNA coding region, more preferably at least about 95% identical, and even more preferably at least about 99% identical.

According to a further aspect of the invention, the viral construct also comprises a nucleotide sequence encoding a gene of interest. The gene of interest is preferably operably linked to a Polymerase II promoter. Such a construct also can contain, for example, an enhancer sequence operably linked with the Polymerase II promoter.

A variety of Polymerase II promoters can be used with the invention, including for example, the CMV promoter. The RNA Polymerase II promoter that is chosen can be a ubiquitous promoter, capable of driving expression in most tissues, for example, the human Ubiquitin-C promoter, CMV β-actin promoter or PGK promoter. In other embodiments the RNA Polymerase II promoter is a tissue-specific promoter.

In one embodiment, the gene of interest is a marker or reporter gene, that can be used to verify that the vector was successfully transfected or transduced and its sequences expressed. In one such embodiment, the gene of interest is a fluorescent reporter gene, for example, the Green Fluorescent Protein. In yet another embodiment, the gene of interest is a drug resistant gene which can be used to select the cells that are successfully transduced. For example, the drug resistant gene can be the zeocin resistant gene (zeo). The gene of interest also can be a hybrid of a drug resistant gene and a fluorescent reporter gene, such as a zeo/gfp fusion. In another embodiment, the gene of interest encodes a protein factor that can regulate the transcription activity of inducible pol III promoters. In one of such embodiment, the gene of interest is tetR (repressor for tet operon) which regulates tetracycline responsive pol III promoters.

It is another aspect of the invention to provide methods for expressing an RNA molecule or molecules within a cell. According to the invention, a packaging cell line is transfected with a retroviral construct of the invention, recombinant retroviral particles are recovered from the packaging cell line; and a target cell is infected with the recombinant retrovirus particles.

In one embodiment of the invention, the target cell is an embryonic cell. An embryonic cell may be, for example, a single cell embryo or embryonic cells from within an early-stage embryo. In another embodiment of the invention, the target cell is an embryogenic stem cell. When the target cell is an embryonic cell, in one embodiment the embryonic cell is infected by injecting the recombinant retrovirus between the zona pellucida and the cell membrane of the embryonic cell. In another embodiment, the embryonic cell is infected by removing the zona pellucida and incubating the cell in solution containing the recombinant retrovirus. In such an embodiment, the zona pellucida can be removed, for example, by enzymatic digestion.

When the target cell is an embryonic cell or an embryogenic stem cell, the cell may be transplanted in a pseudopregnant female to generate a transgenic animal.

The methods of the invention also can be used with a variety of primary ex vivo normal or diseased cells or cells adapted in various tissue culture conditions from human, mouse and other vertebrates, including, without limitation, stem or precursor cells for the hematopoietic system, central nerve system cells, cells with regenerative capacities from a variety of other tissues and organs, dendritic cells and other developing and mature myeloid and lymphoid cells, and cancer cells derived from different cell lineages.

In a particular embodiment, the target cell is an embryonic cell of a bird within an egg. The embryonic cell of a bird is preferably infected by contacting the embryonic blastodisc of the bird egg with retroviral particles.

In yet another embodiment, the target cell is a fish egg. The fish egg is preferably infected by delivering the retroviral particles to the space between the chorion and the cell membrane of the fish egg.

DETAILED DESCRIPTION OF THE PREFERRED EMBODIMENT

Figure 1A:
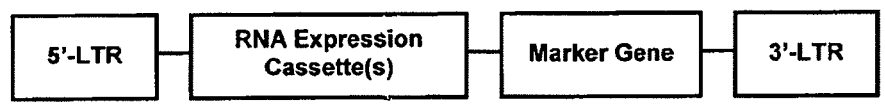
FIG. 1A shows a schematic diagram of a retroviral vector carrying an expression cassette for RNA expression, termed "RNA cassette" and a "Marker Gene" or gene of interest. The RNA expression cassette can be embedded at any permissible sites of the retroviral construct either as single copy or multiple tandem copies. In addition, although not indicated in the figure, more than one RNA expression cassette may be present in the retroviral construct.

The inventors have previously identified a method for introducing a transgene of interest into a cell or animal. This technique is described in co-pending U.S. provisional patent application No. 60/322,031 filed on Sep. 13, 2001 and co-pending U.S. provisional patent application No. 60/347,782 filed on Jan. 9, 2002, the entire contents of which are incorporated herein by reference.

Unless defined otherwise, all technical and scientific terms used herein have the same meaning as commonly understood by one of ordinary skill in the art to which this invention belongs. Any methods, devices and materials similar or equivalent to those described herein can be used in the practice of this invention.

By "transgene" is meant any nucleotide sequence, particularly a DNA sequence, that is integrated into one or more chromosomes of a host cell by human intervention, such as by the methods of the present invention. In one embodiment, a transgene is an "RNA coding region." In another embodiment the transgene comprises a "gene of interest." In other embodiments the transgene can be a nucleotide sequence, preferably a DNA sequence, that is used to mark the chromosome where it has integrated. In this situation, the transgene does not have to comprise a gene that encodes a protein that can be expressed.

A "gene of interest" is a nucleic acid sequence that encodes a protein or other molecule that is desirable for integration in a host cell. In one embodiment, the gene of interest encodes a protein or other molecule the expression of which is desired in the host cell. In this embodiment, the gene of interest is generally operatively linked to other sequences that are useful for obtaining the desired expression of the gene of interest, such as transcriptional regulatory sequences.

A "functional relationship" and "operably linked" mean, without limitation, that the gene is in the correct location and orientation with respect to the promoter and/or enhancer that expression of the gene will be affected when the promoter and/or enhancer is contacted with the appropriate molecules.

An "RNA coding region" is a nucleic acid that can serve as a template for the synthesis of an RNA molecule, such as an siRNA. Preferably, the RNA coding region is a DNA sequence.

A "small interfering RNA" or "siRNA" is a double-stranded RNA molecule that is capable of inhibiting the expression of a gene with which it shares homology. In one embodiment the siRNA may be a "hairpin" or stem-loop RNA molecule, comprising a sense region, a loop region and an antisense region complementary to the sense region. In other embodiments the siRNA comprises two distinct RNA molecules that are non-covalently associated to form a duplex.

The term "transgenic" is used herein to describe the property of harboring a transgene. For instance, a "transgenic organism" is any animal, including mammals, fish, birds and amphibians, in which one or more of the cells of the animal contain nucleic acid introduced by way of human intervention, such as by the methods described herein. In a transgenic animal that comprises a transgene that encodes a gene of interest, the transgene typically causes the cell to express or overexpress a recombinant protein. However, according to the methods of the invention, expression of an RNA coding region can be used to down regulate the expression of a particular gene through antisense or RNA interference mechanisms.

The terms "founder," "founder animal" and "founder line" refer to those animals that are mature products of the embryos or oocytes to which the transgene was added, i.e. those animals that grew from the embryos or oocytes into which DNA was inserted.

The terms "progeny" and "progeny of the transgenic animal" refer to any and all offspring of every generation subsequent to the originally transformed animal.

The term "animal" is used in its broadest sense and refers to all animals including mammals, birds, fish, reptiles and amphibians.

The term "mammal" refers to all members of the class Mammalia and includes any animal classified as a mammal, including humans, domestic and farm animals, and zoo, sports or pet animals, such as mouse, rabbit, pig, sheep, goat, cattle and higher primates.

The term "oocyte" refers to a female gamete cell and includes primary oocytes, secondary oocytes and mature, unfertilized ovum. As used herein, the term "egg" when used in reference to a mammalian egg, means an oocyte surrounded by a zona pellucida. The term "zygote" refers to a fertilized ovum. The term "embryo" broadly refers to an animal in the early stages of development.

"Perivitelline space" refers to the space located between the zona pellucida and the cell membrane of a mammalian egg or embryonic cell.

"Target cell" or "host cell" means a cell that is to be transformed using the methods and compositions of the invention.

"Lentivirus" refers to a genus of retroviruses that are capable of infecting dividing and non-dividing cells. Several examples of lentiviruses include HIV (human immunodeficiency virus; including HIV type 1, and HIV type 2), the etiologic agent of the human acquired immunodeficiency syndrome (AIDS); visna-maedi, which causes encephalitis (visna) or pneumonia (maedi) in sheep, the caprine arthritis-encephalitis virus, which causes immune deficiency, arthritis, and encephalopathy in goats; equine infectious anemia virus, which causes autoimmune hemolytic anemia, and encephalopathy in horses; feline immunodeficiency virus (FIV), which causes immune deficiency in cats; bovine immune deficiency virus (BIV), which causes lymphadenopathy, lymphocytosis, and possibly central nervous system infection in cattle; and simian immunodeficiency virus (SIV), which cause immune deficiency and encephalopathy in sub-human primates.

A lentiviral genome is generally organized into a 5' long terminal repeat (LTR), the gag gene, the pol gene, the env gene, the accessory genes (nef, vif, vpr, vpu) and a 3' LTR. The viral LTR is divided into three regions called U3, R and U5. The U3 region contains the enhancer and promoter elements. The U5 region contains the polyadenylation signals. The R (repeat) region separates the U3 and U5 regions and transcribed sequences of the R region appear at both the 5' and 3' ends of the viral RNA. See, for example, "RNA Viruses: A Practical Approach" (Alan J. Cann, Ed., Oxford University Press, (2000)), O Narayan and Clements J. Gen. Virology 70:1617-1639 (1989), Fields et al. Fundamental Virology Raven Press. (1990), Miyoshi H, Blomer U, Takahashi M, Gage F H, Verma I M. *J. Virol.* 72(10):8150-7 (1998), and U.S. Pat. No. 6,013,516.

Lentiviral vectors are known in the art, including several that have been used to transfect hematopoietic stem cells. Such vectors can be found, for example, in the following publications, which are incorporated herein by reference: Evans J T et al. *Hum Gene Ther* 1999; 10:1479-1489; Case S S, Price M A, Jordan C T et al. *Proc Natl Acad Sci USA* 1999; 96:2988-2993; Uchida N, Sutton R E, Friera A M et al. Proc Natl Acad Sci USA 1998; 95:11939-11944; Miyoshi H, Smith K A, Mosier D E et al. *Science* 1999; 283:682-686; Sutton R E, Wu H T, Rigg R et al. Human immunodeficiency virus type 1 vectors efficiently transduce human hematopoietic stem cells. *J Virol* 1998; 72:5781-5788.

"Virion," "viral particle" and "retroviral particle" are used herein to refer to a single virus comprising an RNA genome, pol gene derived proteins, gag gene derived proteins and a lipid bilayer displaying an envelope (glyco)protein. The RNA genome is usually a recombinant RNA genome and thus may contain an RNA sequence that is exogenous to the native viral genome. The RNA genome may also comprise a defective endogenous viral sequence.

A "pseudotyped" retrovirus is a retroviral particle having an envelope protein that is from a virus other than the virus from which the RNA genome is derived. The envelope protein may be from a different retrovirus or from a non-retroviral virus. A preferred envelope protein is the vesicular stomatitius virus G (VSV G) protein. However, to eliminate the possibility of human infection, viruses can alternatively be pseudotyped with ecotropic envelope protein that limit infection to a specific species, such as mice or birds. For example, in one embodiment, a mutant ecotropic envelope protein is used, such as the ecotropic envelope protein 4.17 (Powell et al. Nature Biotechnology 18(12):1279-1282 (2000)).

The term "provirus" is used to refer to a duplex DNA sequence present in a eukaryotic chromosome that corresponds to the genome of an RNA retrovirus. The provirus may be transmitted from one cell generation to the next without causing lysis or destruction of the host cell.

A "self-inactivating 3' LTR" is a 3' long terminal repeat (LTR) that contains a mutation, substitution or deletion that prevents the LTR sequences from driving expression of a downstream gene. A copy of the U3 region from the 3' LTR acts as a template for the generation of both LTR's in the integrated provirus. Thus, when the 3' LTR with an inactivating deletion or mutation integrates as the 5' LTR of the provirus, no transcription from the 5' LTR is possible. This eliminates competition between the viral enhancer/promoter and any internal enhancer/promoter. Self-inactivating 3' LTRs are described, for example, in Zufferey et al. *J. Virol.* 72:9873-9880 (1998), Miyoshi et al. *J. Virol.* 72:8150-8157 and Iwakuma et al. *Virology* 261:120-132 (1999).

The term "RNA interference or silencing" is broadly defined and includes all posttranscriptional and transcriptional mechanisms of RNA mediated inhibition of gene expression, such as those described in (P. D. Zamore *Science* 296, 1265 (2002)).

In one aspect of the invention, a recombinant retrovirus is used to deliver a transgene comprising an RNA coding region of interest to a target cell. Preferably the target cell is a mammalian cell. The cell may be a primary cell, or may be a cultured cell, for example an without limitation an HEK, CHO, COS, MEF, 293 cell. In one embodiment the target cell is an oocyte or an embryonic cell, more preferably a one-cell embryo. The RNA coding region and any associated genetic elements are thus integrated into the genome of the target cell as a provirus. When the target cell is an embryo, the cell may then be allowed to develop into a transgenic animal by methods well known in the art.

The recombinant retrovirus used to deliver the RNA coding region is preferably a modified lentivirus, and thus is able to infect both dividing and non-dividing cells. The recombinant retrovirus preferably comprises a modified lentiviral genome that includes the transgene. Further, the modified lentiviral genome preferably lacks endogenous genes for proteins required for viral replication, thus preventing undesired replication, such as replication in a resulting transgenic animal. The required proteins are preferably provided in trans in the packaging cell line during production of the recombinant retrovirus, as described below.

In another embodiment, the recombinant retrovirus used to deliver the RNA coding region is a modified Moloney virus, for example a Moloney Murine Leukemia Virus. In a further embodiment, the virus is a Murine Stem Cell Virus (Hawley, R. G., et al. (1996) Proc. Natl. Acad. Sci. USA 93:10297-10302; Keller, G., et al. (1998) Blood 92:877-887; Hawley, R. G., et al. (1994) Gene Ther. 1:136-138). The recombinant retrovirus also can be a hybrid virus such as that described in Choi, J K; Hoanga, N; Vilardi, A M; Conrad, P; Emerson, S G;

Gewirtz, A M. (2001) Hybrid HIV/MSCV LTR Enhances Transgene Expression of Lentiviral Vectors in Human CD34+ Hematopoietic Cells. *Stem Cells* 19, No. 3, 236-246.

In the preferred embodiment the transgene is incorporated into a viral construct that comprises an intact retroviral 5' LTR and a self-inactivating 3' LTR. The viral construct is preferably introduced into a packaging cell line that packages viral genomic RNA based on the viral construct into viral particles with the desired host specificity. Viral particles are collected and used to infect the host cell. Each of these aspects is described in detail below.

The Viral Construct

The viral construct is a nucleotide sequence that comprises sequences necessary for the production of recombinant retrovirus in a packaging cell. In one embodiment the viral construct additionally comprises genetic elements that allow for the desired expression of an RNA molecule or gene of interest in the host.

Generation of the viral construct can be accomplished using any suitable genetic engineering techniques well known in the art, including, without limitation, the standard techniques of PCR, oligonucleotide synthesis, restriction endonuclease digestion, ligation, transformation, plasmid purification, and DNA sequencing, for example as described in Sambrook et al. (Molecular Cloning: A Laboratory Manual. Cold Spring Harbor Laboratory Press, N.Y. (1989)), Coffin et al. (Retroviruses. Cold Spring Harbor Laboratory Press, N.Y. (1997)) and "RNA Viruses: A Practical Approach" (Alan J. Cann, Ed., Oxford University Press, (2000)).

The viral construct may incorporate sequences from the genome of any known organism. The sequences may be incorporated in their native form or may be modified in any way. For example, the sequences may comprise insertions, deletions or substitutions. In the preferred embodiment the viral construct comprises sequences from a lentivirus genome, such as the HIV genome or the SIV genome.

The viral construct preferably comprises sequences from the 5' and 3' LTRs of a lentivirus. More preferably the viral construct comprises the R and U5 sequences from the 5' LTR of a lentivirus and an inactivated or self-inactivating 3' LTR from a lentivirus. The LTR sequences may be LTR sequences from any lentivirus from any species. For example, they may be LTR sequences from HIV, SIV, FIV or BIV. Preferably the LTR sequences are HIV LTR sequences. The virus also can incorporate sequences from MMV or MSCV.

The viral construct preferably comprises an inactivated or self-inactivating 3' LTR. The 3' LTR may be made self-inactivating by any method known in the art. In the preferred embodiment the U3 element of the 3' LTR contains a deletion of its enhancer sequence, preferably the TATA box, Sp1 and NF-kappa B sites. As a result of the self-inactivating 3' LTR, the provirus that is integrated into the host cell genome will comprise an inactivated 5' LTR.

Optionally, the U3 sequence from the lentiviral 5' LTR may be replaced with a promoter sequence in the viral construct. This may increase the titer of virus recovered from the packaging cell line. An enhancer sequence may also be included. Any enhancer/promoter combination that increases expression of the viral RNA genome in the packaging cell line may be used. In the preferred embodiment the CMV enhancer/promoter sequence is used (U.S. Pat. No. 5,168,062; Karasuyama et al J. Exp. Med. 169:13 (1989).

Figure 1B:
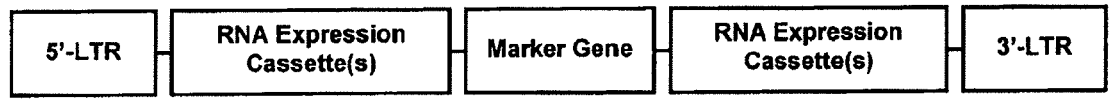
FIG. 1B shows a similar construct in which the RNA expression cassettes flank a marker gene.

The viral construct also comprises a transgene. The transgene, may be any nucleotide sequence, including sequences that serve as markers for the provirus. Preferably the transgene comprises one or more RNA coding regions and/or one or more genes of interest. Schematic diagrams of exemplary retroviral constructs are shown in FIGS. 1A and 1B.

In the preferred embodiment the transgene comprises at least one RNA coding region. Preferably the RNA coding region is a DNA sequence that can serve as a template for the expression of a desired RNA molecule in the host cell. In one embodiment, the viral construct comprises two or more RNA coding regions.

The viral construct also preferably comprises at least one RNA Polymerase III promoter. The RNA Polymerase III promoter is operably linked to the RNA coding region and can also be linked to a termination sequence. In addition, more than one RNA Polymerase III promoter may be incorporated.

RNA Polymerase III promoters are well known to one of skill in the art. A suitable range of RNA Polymerase III promoters can be found, for example, in Paule and White. *Nucleic Acids Research.*, Vol 28, pp 1283-1298 (2000), which is hereby incorporated by reference in its entirety. The definition of RNA Polymerase III promoters also include any synthetic or engineered DNA fragment that can direct RNA Polymerase III to transcribe a downstream RNA coding sequence. Further, the RNA Polymerase III (Pol III) promoter or promoters used as part of the viral vector can be inducible. Any suitable inducible Pol III promoter can be used with the methods of the invention. Particularly suited Pol III promoters include the tetracycline responsive promoters provided in Ohkawa and Taira *Human Gene Therapy*, Vol. 11, pp 577-585 (2000) and in Meissner et al. *Nucleic Acids Research*, Vol. 29, pp 1672-1682 (2001), which are incorporated herein by reference.

In one embodiment the transgene comprises a gene of interest that encodes a protein that is desirably expressed in one or more cells of a transgenic animal, for example, a reporter or marker protein. Preferably the gene of interest is located between the 5' LTR and 3' LTR sequences. Further, the gene of interest is preferably in a functional relationship with other genetic elements, for example transcription regulatory sequences such as promoters and/or enhancers, to regulate expression of the gene of interest in a particular manner once the transgene is incorporated into the host genome. In certain embodiments, the useful transcriptional regulatory sequences are those that are highly regulated with respect to activity, both temporally and spatially.

Preferably the gene of interest is in a functional relationship with internal Polymerase II promoter/enhancer regulatory sequences. An "internal" promoter/enhancer is one that is located between the 5' LTR and the 3' LTR sequences in the viral construct and is operably linked to the gene that is desirably expressed.

The Polymerase II promoter/enhancer may be any promoter, enhancer or promoter/enhancer combination known to increase expression of a gene with which it is in a functional relationship.

The internal promoter/enhancer is preferably selected based on the desired expression pattern of the gene of interest and the specific properties of known promoters/enhancers. Thus, the internal promoter may be a constitutive promoter. Non-limiting examples of constitutive promoters that may be used include the promoter for ubiquitin, CMV (U.S. Pat. No. 5,168,062; Karasuyama et al J. Exp. Med. 169:13 (1989), β-actin (Gunning et al. Proc. Natl. Acad. Sci. USA 84:4831-4835 (1987) and pgk (see, for example, U.S. Pat. Nos. 4,615,974 and 5,104,795; Adra et al. Gene 60:65-74 (1987), Singer-Sam et al. Gene 32:409-417 (1984) and Dobson et al. Nucleic Acids Res. 10:2635-2637 (1982)). Alternatively, the promoter may be a tissue specific promoter. Several non-limiting examples of tissue specific promoters that may be used include lck (see, for example, Garvin et al. Mol. Cell. Biol. 8:3058-3064 (1988) and Takadera et al. Mol. Cell. Biol. 9:2173-2180 (1989)), myogenin (Yee et al. Genes and Development 7:1277-1289 (1993), and thy 1 (Gundersen et al. Gene 113:207-214 (1992). In addition, promoters may be selected to allow for inducible expression of the transgene. A number of systems for inducible expression using such a promoter are known in the art, including the tetracycline responsive system and the lac operator-repressor system. It is also contemplated that a combination of promoters may be used to obtain the desired expression of the gene of interest. The skilled artisan will be able to select a promoter based on the desired expression pattern of the gene in the resulting transgenic animal.

An internal enhancer may also be present in the viral construct to increase expression of the gene of interest. For example the CMV enhancer (Karasuyama et al J. Exp. Med. 169:13 (1989) may be used in combination with the chicken β-actin promoter (see, e.g., JP 1990005890-A1). Again, one of skill in the art will be able to select the appropriate enhancer based on the desired expression pattern.

The gene of interest is not limited in any way and includes any gene that the skilled practitioner desires to have integrated and/or expressed in a transgenic animal. For example, the gene of interest may be one that encodes a protein that serves as a marker to identify cells comprising the provirus. In other embodiments the gene of interest encodes a protein that modifies a physical characteristic of the transgenic animal, such as a protein that modifies size, growth, or tissue composition. In another example the gene of interest may encode a protein of commercial value that may be harvested from the transgenic animal.

In addition, more than one gene of interest may be placed in functional relationship with the internal promoter. For example a gene encoding a marker protein may be placed after the primary gene of interest to allow for identification of cells that are expressing the desired protein. In one embodiment a fluorescent marker protein, preferably green fluorescent protein (GFP), is incorporated into the construct along with the gene of interest. If a second reporter gene is included, an internal ribosomal entry site (IRES) sequence is also preferably included (U.S. Pat. No. 4,937,190). The IRES sequence may facilitate the expression of the reporter gene.

The viral construct may also contain additional genetic elements. The types of elements that may be included in the construct are not limited in any way and will be chosen by the skilled practitioner to achieve a particular result. For example, a signal that facilitates nuclear entry of the viral genome in the target cell may be included. An example of such a signal is the HIV-1 flap signal.

Further, elements may be included that facilitate the characterization of the provirus integration site in the genome of the animal. For example, a tRNA amber suppressor sequence may be included in the construct.

In addition, the construct may contain one or more genetic elements designed to enhance expression of the gene of interest. For example, a woodchuck hepatitis virus responsive element (WRE) may be placed into the construct (Zufferey et al. J. Virol. 74:3668-3681 (1999); Deglon et al. Hum. Gene Ther. 11:179-190 (2000)).

A chicken β-globin insulator (Chung et al. Proc. Natl. Acad. Sci. USA 94:575-580 (1997)) may also be included in the viral construct. This element has been shown to reduce the chance of silencing the integrated provirus in the transgenic animal due to methylation and heterochromatinization effects. In addition, the insulator may shield the internal enhancer, promoter and exogenous gene from positive or negative positional effects from surrounding DNA at the integration site on the chromosome.

Any additional genetic elements are preferably inserted 3' of the gene of interest.

In a specific embodiment, the viral vector comprises: a cytomegalovirus (CMV) enhancer/promoter sequence; the R and U5 sequences from the HIV 5' LTR; the HIV-1 flap signal; an internal enhancer; an internal promoter; a gene of interest; the woodchuck hepatitis virus responsive element; a tRNA amber suppressor sequence; a U3 element with a deletion of its enhancer sequence; the chicken β-globin insulator; and the R and U5 sequences of the 3' HIV LTR.

The viral construct is preferably cloned into a plasmid that may be transfected into a packaging cell line. The preferred plasmid preferably comprises sequences useful for replication of the plasmid in bacteria.

Production of Virus

Any method known in the art may be used to produce infectious retroviral particles whose genome comprises an RNA copy of the viral construct described above.

Preferably, the viral construct is introduced into a packaging cell line. The packaging cell line provides the viral proteins that are required in trans for the packaging of the viral genomic RNA into viral particles. The packaging cell line may be any cell line that is capable of expressing retroviral proteins. Preferred packaging cell lines include 293 (ATCC CCL X), HeLa (ATCC CCL 2), D17 (ATCC CCL 183), MDCK (ATCC CCL 34), BHK (ATCC CCL-10) and Cf2Th (ATCC CRL 1430). The most preferable cell line is the 293 cell line.

The packaging cell line may stably express the necessary viral proteins. Such a packaging cell line is described, for example, in U.S. Pat. No. 6,218,181. Alternatively a packaging cell line may be transiently transfected with plasmids comprising nucleic acid that encodes the necessary viral proteins.

In one embodiment a packaging cell line that stably expresses the viral proteins required for packaging the RNA genome is transfected with a plasmid comprising the viral construct described above.

In another embodiment a packaging cell line that does not stably express the necessary viral proteins is co-transfected with two or more plasmids essentially as described in Yee et al. (Methods Cell. Biol. 43A, 99-112 (1994)). One of the plasmids comprises the viral construct comprising the transgene. The other plasmid(s) comprises nucleic acid encoding the proteins necessary to allow the cells to produce functional virus that is able to infect the desired host cell.

The packaging cell line may not express envelope gene products. In this case the packaging cell line will package the viral genome into particles that lack an envelope protein. As the envelope protein is responsible, in part, for the host range of the viral particles, the viruses are preferably pseudotyped. Thus the packaging cell line is preferably transfected with a plasmid comprising sequences encoding a membrane-associated protein that will permit entry of the virus into a host cell. One of skill in the art will be able to choose the appropriate pseudotype for the host cell that is to be used. For example, in one embodiment the viruses are pseudotyped with the vesicular stomatitis virus envelope glycoprotein (VSVg). In addition to conferring a specific host range this pseudotype may permit the virus to be concentrated to a very high titer. Viruses can alternatively be pseudotyped with ecotropic envelope proteins that limit infection to a specific species, such as mice or birds. For example, in another embodiment, a mutant ecotropic envelope protein is used, such as the ecotropic envelope protein 4.17 (Powell et al. Nature Biotechnology 18(12):1279-1282 (2000)).

In the preferred embodiment a packaging cell line that does not stably express viral proteins is transfected with the viral construct, a second vector comprising the HIV-1 packaging vector with the env, nef, 5'LTR, 3'LTR and vpu sequences deleted, and a third vector encoding an envelope glycoprotein. Preferably the third vector encodes the VSVg envelope glycoprotein.

In another embodiment of invention, RNA interference activity of the packaging cells is suppressed to improve the production of recombinant virus. This includes, without limitation, the use of cotransfection or stable transfection of constructs expressing siRNA molecules to inhibit Dicer, an RNase III family member of ribonuclease which is essential for RNA interference (Hammond et al. Nat. Rev. Genet. 2:110-119 (2001)).

The recombinant virus is then preferably purified from the packaging cells, titered and diluted to the desired concentration.

Transgenic Animals

In order to make transgenic animals, an oocyte or one or more embryonic cells are infected with the recombinant virus produced as described above. One of skill in the art will recognize that the method of infection and the treatment of the cell following infection will depend upon the type of animal from which the cell is obtained. For example, mammalian cells are preferably implanted in a pseudopregnant female following infection while for the generation of transgenic birds or fish, the virus is preferably delivered to a laid egg and thus implantation is not required.

While early methods of making transgenic animals required the cells to be rapidly dividing, there is no such requirement in the methods of the present invention. Thus the cell may be contacted at any point in development. In the preferred embodiment, a zygote is contacted with the recombinant virus.

The cells to be infected with the virus may be obtained by any method known in the art and appropriate for the specific species in which it is desired to make a transgenic animal. For example, the recovery of fertilized mouse oocytes is described in Hogan et al. (Manipulating the Mouse Embryo: A Laboratory Manual. $2^{nd}$ ed. Cold Spring Harbor Laboratory Press, NY (1994)). A method for obtaining fertilized rat oocytes is described in Armstrong et al. (Biol. Reprod. 39, 511-518 (1998)).

It is not necessary that the cells be contacted after fertilization. In one embodiment, the virus is delivered to unfertilized ova. Development may then be initialized, for example by in vitro fertilization.

Delivery of the Virus

The virus may be delivered to the cell in any way that allows the virus to infect the cell. Preferably the virus is allowed to contact the cell membrane. Two preferred methods of delivering the virus to mammalian cells, injection and direct contact, are described below.

Injection

In a first embodiment the virus is injected into the perivitelline space between the zona pellucida and the cell membrane of a single-cell zygote. Preferably less than 50 picoliters of viral suspension is injected, more preferably less than 25 picoliters and even more preferably about 10 picoliters.

The virus is preferably present in a viral suspension and may be injected by any method known in the art. The viral suspension is preferably injected through a hydraulic injector. More preferably a glass micropipette is used to inject the virus. In one embodiment a micropipette is prepared by pulling borosilicate glass capillary on a pipette puller. The tip is preferably opened and beveled to approximately 10 μm. The lentiviral suspension may be loaded into the micropipette from the tip using gentle negative pressure.

In one embodiment the cell is stabilized with a holding pipette mounted on a micromanipulator, such as by gentle negative pressure against a fire-polished pipette, and a second micromanipulator is used to direct the tip of a micropipette into the space between the zona pellucida and the cell membrane, where the virus is injected.

Direct Contact

In another embodiment the zona pellucida is removed from the cell to produce a denuded embryo and the cell membrane is contacted with the virus. The zona pellucida may be removed by any method known in the art. Preferably it is removed by enzymatic treatment. For example, treatment with pronase may be used to remove the zona pellucida while the cell membrane is kept intact. Alternatively, the cell may be placed in media at pH at which the zona pellucida dissolves while the cell membrane remains intact. For example the cell may be incubated in an acidic Tyrode's solution at room temperature for several minutes. Once the zona pellucida is removed, any method that allows for the virus to contact the cell membrane may be used. Preferably, the cell is incubated in a solution containing the virus. Even more preferably, the solution is media that facilitates survival of the cell.

In this embodiment, the cells are preferably contacted with the virus in culture plates. The virus may be suspended in media and added to the wells of a multi-well culture plate. The cells may then be plated in the individual wells. The media containing the virus may be added prior to the plating of the cells or after the cells have been plated. Preferably individual cells are incubated in approximately 10 μl of media. However, any amount of media may be used as long as an appropriate concentration of virus in the media is maintained such that infection of the host cell occurs.

The cells are preferably incubated with the virus for a sufficient amount of time to allow the virus to infect the cells. Preferably the cells are incubated with virus for at least 1 hour, more preferably at least 5 hours and even more preferably at least 10 hours.

Both the injection and direct contact embodiments may advantageously be scaled up to allow high throughput transgenesis. Because of the relative simplicity of the injection technique, it is possible to inject many embryos rapidly. For example, it is possible to inject more than 200 fertilized oocytes in less than one hour. With regard to the direct contact embodiment, any number of embryos may be incubated in the viral suspension simultaneously. This may be accomplished, for example, by plating the desired number of single-cell zygotes in multi-well tissue culture plates containing the virus suspended in media appropriate for the survival and growth of the cells.

In both embodiments, any concentration of virus that is sufficient to infect the cell may be used. Preferably the concentration is at least 1 pfu/μl, more preferably at least 10 pfu/μl, even more preferably at least 400 pfu/μl and even more preferably at least $1 \times 10^4$ pfu/μl.

Following infection with the virus, the cells are preferably implanted in an animal. More preferably cells infected with the virus are implanted in pseudopregnant animals of the same species from which the infected cells were obtained. Methods of creating pseudo-pregnancy in animals and implanting embryos are well known in the art and are described, for example, in Hogan et al. (Manipulating the Mouse Embryo: A Laboratory Manual. $2^{nd}$ ed. Cold Spring Harbor Laboratory Press, NY (1994)).

In the preferred embodiment early stage embryos (approximately 0-2.5 days p.c.) still with an intact zona pellucida are transferred to the oviduct of timed pseudopregnant female (preferably 0.5 days p.c.), while embryos that have reached the blastocyst stage are transferred to the uterus of timed pseudopregnant females (preferably 2.5 days p.c.). Denuded embryos are preferably cultured in vitro until they reach the morula or blastocyst stage (48 to 72 hours in culture), and are then implanted into appropriately timed pseudopregnant females.

The embryos and resulting animals may be analyzed, for example for integration of the transgene, the number of copies of the transgene that integrated, the location of the integration, the ability to transmit the transgene to progeny and expression of the transgene. Such analysis may be carried out at any time and may be carried out by any methods known in the art. Standard techniques are described, for example, in Hogan et al. (supra).

The methods of infecting cells disclosed above do not depend upon species-specific characteristics of the cells. As a result, they are readily extended to all mammalian species.

Initial experiments with mice indicate that of those animals that develop to full term, 80-90% carried at least one copy of the transgene and that, of these, approximately 85% express the gene of interest. Of the transgenic animals about 25% carry only 1 or 2 copies of the transgene. The highest number of proviral insertions observed was about 30. Of the animals that carried only 1 or 2 copies of the transgene, about 80% expressed the gene of interest.

As discussed above, the modified retrovirus can be pseudotyped to confer upon it a broad host range. One of skill in the art would also be aware of appropriate internal promoters to achieve the desired expression of a gene of interest in a particular animal species. Thus, one of skill in the art will be able to modify the method of infecting cells to create transgenic animals of any species.

In one embodiment, transgenic birds are created by delivering a modified retrovirus, as described above, to the primordial germ cells of early stage avian embryos. Freshly laid eggs are obtained and placed in a temperature controlled, humidified incubator. Preferably, the embryonic blastodisc in the egg is gradually rotated to lie on top of the yolk. This may be accomplished by any method known in the art, such as by gently rocking the egg regularly, preferably every 15 minutes. Approximately 36 hours later, the modified retrovirus is delivered into the space between the embryonic disk and the perivitelline membrane. Preferably about 50 nL of viral solution is delivered, more preferably about 100 nL of viral solution is delivered, and even more preferably about 200 nL of viral solution is delivered. The viral solution may be delivered by any method known in the art for delivering compositions to the inside of an egg. In the preferred embodiment a window is opened in the shell, the viral solution is injected through the window and the shell window is closed. The eggs are preferably incubated until hatching. The eggs will hatch after approximately 20 days, depending upon the particular avian species from which they are obtained. Hatched chicks are preferably raised to sexual maturity and mated. The transgenic offspring of the founder animals may be identified by any method known in the art, such as Southern blot, PCR and expression analysis.

In another embodiment, transgenic fish are created by delivering the modified retrovirus, described above, to single-cell fish embryos. Fertilized fish eggs are collected by any method known in the art. The modified retrovirus is then preferably delivered to the space between the chorion and the cell membrane. This may be accomplished, for example, by loading the modified retrovirus in solution into a glass pipette. The pipette may then be used to pierce the chorion membrane and deliver the viral suspension. Preferably about 50 nL of viral solution is delivered, more preferably about 100 nL of viral solution is delivered, and even more preferably about 200 nL of viral solution is delivered. Injected embryos are preferably returned to a temperature-controlled water tank and allowed to mature. At sexual maturity the founder fish are preferably mated and their progeny analyzed for the presence of the transgene by any method known in the art.

As mentioned above, the methods of the present invention will also prove useful in techniques for identifying genes that are involved in specific biological processes, such as gene trap assays and large-scale mutagenesis screens. Such methods are described in the copending provisional patent applications 60/322,031 filed on Sep. 13, 2001 and copending U.S. provisional patent application 60/347,782 filed on Jan. 9, 2002.

Down-Regulating Gene Expression in a Target Cell

The methods described herein allow the expression of RNA molecules in cells, and are particularly suited to the expression of small RNA molecules, which can not be readily expressed from a Pol II promoter. According to a preferred embodiment of the invention, an RNA molecule is expressed within a cell in order to down-regulate the expression of a target gene. The ability to down-regulate a target gene has many therapeutic and research applications, including identifying the biological functions of particular genes. Using the techniques and compositions of the invention, it will be possible to knock-down (or down-regulate) the expression of a large number of genes, both in cell culture and in mammalian organisms.

In preferred embodiments of the invention, an RNA expression cassette comprises a Pol III promoter and an RNA coding region. The RNA coding region preferably encodes an RNA molecule that is capable of down-regulating the expression of a particular gene or genes. The RNA molecule encoded can, for example, be complementary to the sequence of an RNA molecule encoding a gene to be down-regulated. In such an embodiment, the RNA molecule preferably acts through an antisense mechanism.

A more preferred embodiment involves the expression of a double-stranded RNA complex, or an RNA molecule having a stem-loop or a so-called "hairpin" structure. As used herein, the term "RNA duplex" refers to the double stranded regions of both the RNA complex and the double-stranded region of the hairpin or stem-lop structure.

Double stranded RNA has been shown to inhibit gene expression of genes having a complementary sequence through a process termed RNA interference or suppression (see, for example, Hammond et al. Nat. Rev. Genet. 2:110-119 (2001)).

According to the invention, an RNA duplex or siRNA corresponding to a region of a gene to be down-regulated is expressed in the cell. The RNA duplex is substantially identical (typically at least about 80% identical, more preferably at least about 90% identical) in sequence to the sequence of the gene targeted for down regulation. siRNA duplexes are described, for example, in Bummelkamp et al. Science 296:550-553 (2202), Caplen et al. Proc. Natl. Acad. Sci. USA 98:9742-9747 (2001) and Paddison et al. Genes & Devel. 16:948-958 (2002).

The RNA duplex is generally at least about 15 nucleotides in length and is preferably about 15 to about 30 nucleotides in length. However, a significantly longer RNA duplex can be used effectively in some organisms. In a more preferred embodiment, the RNA duplex is between about 19 and 22 nucleotides in length. The RNA duplex is preferably identical to the target nucleotide sequence over this region.

When the gene to be down regulated is in a family of highly conserved genes, the sequence of the duplex region can be chosen with the aid of sequence comparison to target only the desired gene. On the other hand, if there is sufficient identity among a family of homologous genes within an organism, a duplex region can be designed that would down regulate a plurality of genes simultaneously.

Figure 2:
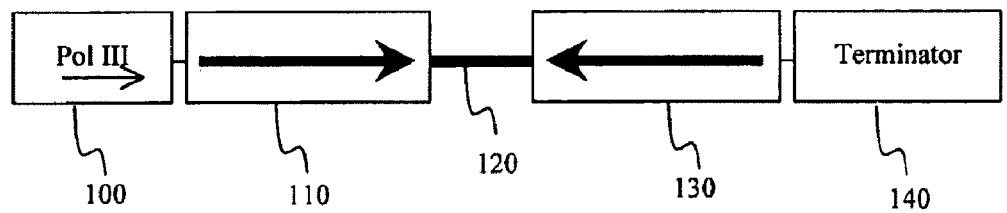
FIG. 2 shows a schematic view of an RNA expression cassette comprising an RNA Polymerase III promoter 100 linked to an RNA coding region 110-130 and a terminator sequence 140. The RNA coding region comprises a sense region 110, a loop region 120, and an antisense region 130.

The duplex RNA can be expressed in a cell from a single retroviral construct. In the preferred embodiment, a single RNA coding region in the construct is a serves as a template for the expression of a self-complementary hairpin RNA, comprising a sense region, a loop region and an antisense region. This embodiment is illustrated in FIG. 2, which shows a schematic view of an RNA expression cassette having an RNA Pol III promoter 100 operatively linked to an RNA coding region, having a sense region 110, a loop region 120, an antisense region 130 and a terminator region 140. The sense 110 and antisense 130 regions are each preferably about 15 to about 30 nucleotides in length. The loop region 120 preferably is about 2 to about 15 nucleotides in length, more preferably from about 4 to about 9 nucleotides in length. Following expression the sense and antisense regions form a duplex.

Figure 3:
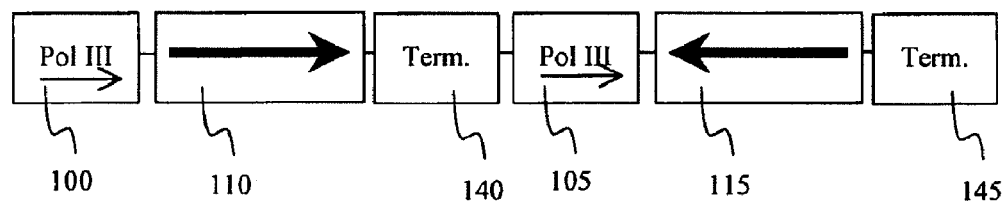
FIG. 3 shows a schematic view of an RNA expression cassette having an RNA Polymerase III promoter 100 linked to a first RNA coding region 110 and a first terminator sequence 140 and a second RNA polymerase III promoter 105 linked to a second RNA coding region 115 and a second terminator 145.

In another embodiment, the retroviral construct comprises two RNA coding regions. The first coding region is a template for the expression of a first RNA and the second coding region is a template for the expression of a second RNA. Following expression, the first and second RNA's form a duplex. The retroviral construct preferably also comprises a first Pol III promoter operably linked to the first RNA coding region and a second Pol III promoter operably linked to the second RNA coding region. This embodiment is illustrated in FIG. 3, which shows a schematic view of an RNA expression cassette having an RNA Polymerase III promoter 100 linked to a first RNA coding region 110 and a first terminator sequence 140 and a second RNA polymerase III promoter 105 linked to a second RNA coding region 115 and a second terminator 145.

Figure 4:
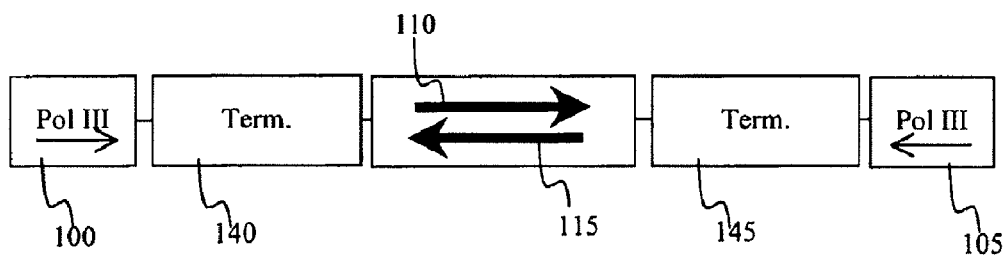
FIG. 4 shows a schematic view of an RNA expression cassette having a first RNA Polymerase III promoter 100 linked to an RNA coding region 110 and a first terminator sequence 145. The expression cassette has a second RNA polymerase III promoter 105 linked to the RNA coding region 115, the same sequence as 110 in reverse, and a second terminator 140.

In yet another embodiment of the invention, the retroviral construct comprises a first RNA Pol III promoter operably linked to a first RNA coding region, and a second RNA Pol III promoter operably linked to the same first RNA coding region in the opposite direction, such that expression of the RNA coding region from the first RNA Pol III promoter results in a synthesis of a first RNA molecule as the sense strand and expression of the RNA coding region from the second RNA Pol III promoter results in synthesis of a second RNA molecule as an antisense strand that is substantially complementary to the first RNA molecule. In one such embodiment, both RNA Polymerase III promoters are separated from the RNA coding region by termination sequences, preferably termination sequences having five consecutive T residues. FIG. 4 shows a schematic view of an RNA expression cassette having a first RNA Polymerase III promoter 100 linked to an RNA coding region 110 and a first terminator sequence 145. The expression cassette has a second RNA polymerase III promoter 105 linked to the RNA coding region 115, the same sequence as 110 in reverse, and a second terminator 140.

In further embodiments an RNA duplex is expressed using two or more retroviral constructs. In one embodiment, a first retroviral construct is used that directs the expression of a first RNA and a second retroviral construct is used that directs expression of a second RNA that is complementary to the first. Following expression the first and second RNAs form a duplex region. It is preferred, however, that the entire duplex region is introduced using retroviral particles derived from a single retroviral construct. As discussed above, several strategies for expressing a duplex RNA from a single viral construct are shown in FIGS. 2-4.

The RNA duplexes may be flanked by single stranded regions on one or both sides of the duplex. For example, in the case of the hairpin, the single stranded loop region would connect the duplex region at one end.

The RNA coding region is generally operatively linked to a terminator sequence. The pol III terminators preferably comprise of stretches of 4 or more thymidine ("T") residues. In a preferred embodiment, a cluster of 5 consecutive Ts is linked immediately downstream of the RNA coding region to serve as the terminator. In such a construct pol III transcription is terminated at the second or third T of the DNA template, and thus only 2 to 3 uridine ("U") residues are added to the 3' end of the coding sequence.

The sequence of the RNA coding region, and thus the sequence of the RNA duplex, preferably is chosen to be complementary to the sequence of a gene whose expression is to be downregulated in a cell or organism. The degree of down regulation achieved with a given RNA duplex sequence for a given target gene will vary by sequence. One of skill in the art will be able to readily identify an effective sequence. For example, in order to maximize the amount of suppression in a transgenic animal, a number of sequences can be tested for their efficacy in cell culture prior to generating a transgenic animal.

The methods of the present invention will find great commercial application, for example in biotechnology, medicine and agriculture. For example, in agriculture the described methods may be used to confer disease resistance by expressing in a cell or organism an siRNA that specifically down-regulates the expression of a gene associated with a pathogen or disease state. In biotechnology, the ability to rapidly develop large numbers of transgenic animals with desired modulation of specific genes will allow for the analysis of gene function and the evaluation of compounds that potentially modulate gene expression, protein function, and are useful in treating a disease or disorder. In particular, by observing the effect of down-regulating specific genes in transgenic animals, the biological function of those genes may be determined. In medicine the methods of the invention may be used to treat patients suffering from particular diseases or disorders, such as HIV, or to confer immunity or resistance to particular pathogens. For example, specific cells may be infected in vivo or ex vivo with recombinant retrovirus encoding an siRNA that down-regulates the activity of a gene whose activity is associated with a particular disease or disorder.

The following examples are offered for illustrative purposes only, and are not intended to limit the scope of the present invention in any way. Indeed, various modifications of the invention in addition to those shown and described herein will become apparent to those skilled in the art from the foregoing description and fall within the scope of the appended claims.

All patent and literature references cited in the present specification are hereby incorporated by reference in their entirety.

EXAMPLES

Example 1

Figure 5:
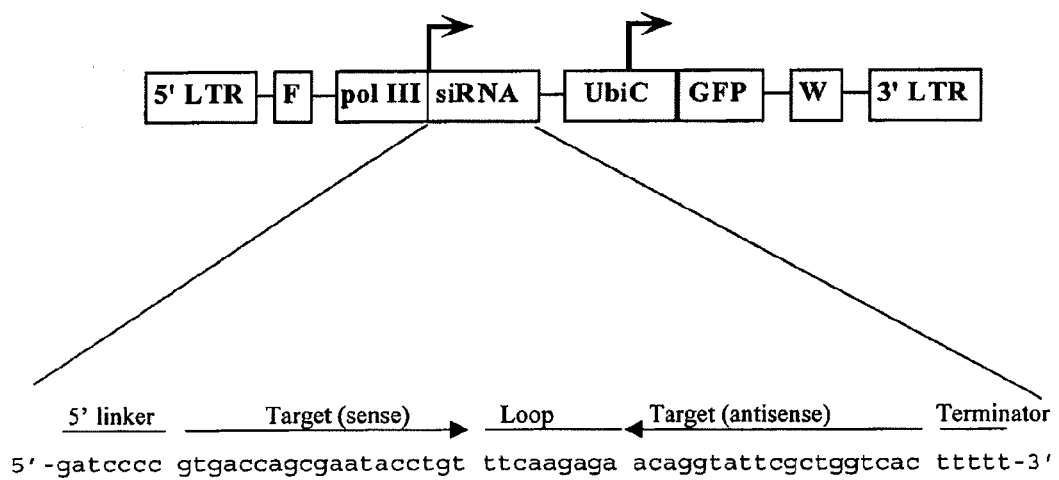
FIG. 5. Schematic illustration of a lacZ siRNA encoding lentiviral vector. 5'LTR: an HIV based lentiviral vector 5' LTR; F: an HIV Flap element; pol III: a human H1-RNA pol III promoter (−240 to −8); siRNA: a lacZ specific small hairpin RNA coding region and its structure and detailed sequence are illustrated below. UbiC: an internal human ubiquitinC promoter; GFP: a GFP marker gene driven by UbiC promoter. W: a woodchuck RNA regulatory element. 3'LTR: an HIV based self inactivating lentiviral 3' LTR.

An lentiviral construct was constructed by insertion of an siRNA expression cassette into the Pad site of HC-FUGW vector (FIG. 5; SEQ ID NO: 2). The siRNA was designed to down-regulate expression of the lacZ gene. The HC-FUGW vector comprised a GFP marker gene operably linked to the human Ubiquitin promoter. The GFP marker was useful for tracking transduction events. The vector also comprised an HIV DNA Flap element to improve the virus titers, and the WRE for high level expression of viral genes. The siRNA expression cassette was composed of a pol III promoter and a small hairpin RNA coding region followed by a pol III terminator site. The pol III promoter (SEQ ID NO:3) was derived from the −240 to −9 region of human H1-RNA promoter and was cloned as an Eco R1 fragment by PCR amplification from HEK293 genomic DNA. The pol III promoter was connected to the downstream RNA coding region by a 7 base pair linker sequence to ensure that the transcription was precisely initiated at the first nucleotide of the RNA coding sequence. The small hairpin RNA coding region comprised a 19 nt sequence corresponding to the 1900-1918 region of the sense strand of the bacterial beta-galactosidase (lacZ) gene coding sequence and the 19 nt perfect reverse complementary sequence separated by a 9 nt loop region. The terminator was comprised of 5 consecutive thymidine residues linked immediately downstream of the RNA coding sequence. The sequence of the hairpin siRNA is shown in SEQ ID NO: 1.

Example 2

Figure 6:
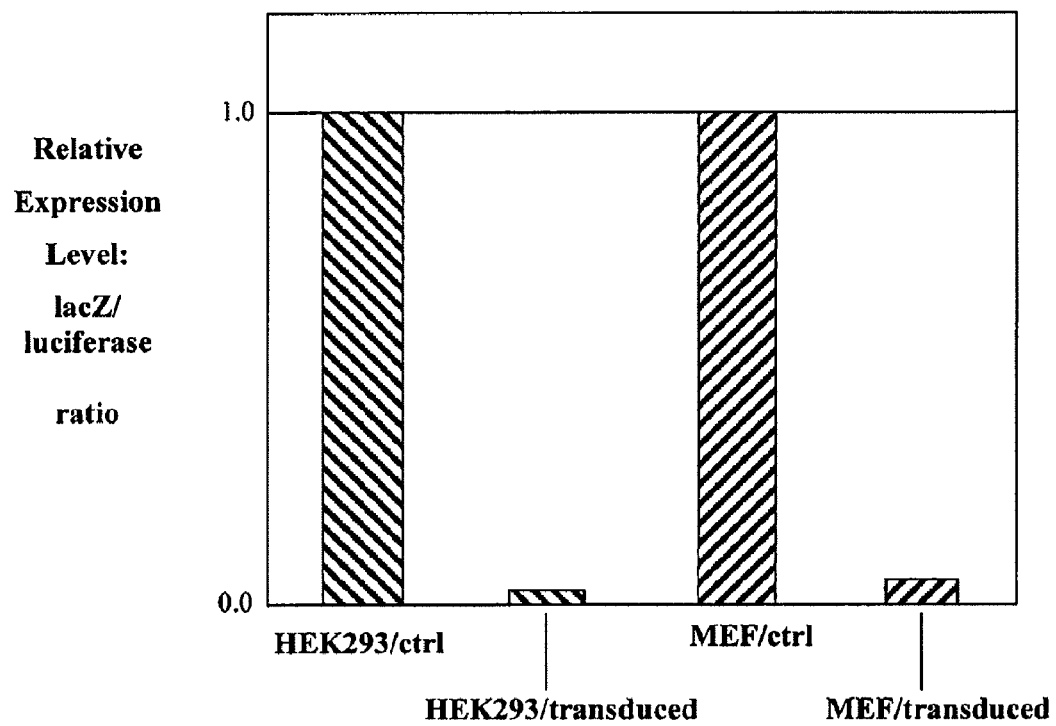
FIG. 6. A lacZ specific siRNA encoded by a lentiviral vector can efficiently inhibit the expression of lacZ reporter gene in virus transduced mammalian cells. MEF: mouse embryonic fibroblasts; HEK293: human embryonic kidney cells. Both of the test cell lines harbor lacZ and firefly luciferase reporter genes, and the expression levels of the reporter genes can be measured by chemiluminescent assays. Ctrl: the ratio of lacZ activity versus Luc activity of the uninfected parental cells, which was arbitrarily set to 1. Transduced: the specific inhibition of lacZ expression calculated as the reduction of lacZ to Luc ratio.

Transduction of cultured mammalian cells with retrovirus derived from the retroviral construct described in Example 1 was achieved (FIG. 6). The retroviral vector encoding a small hairpin RNA molecule described in Example 1, was used to transfect cultured mammalian cells that express lacZ. A profound decrease in the expression of the lacZ was observed.

The lacZ siRNA virus was produced by cotransfection of the retroviral vector, a helper virus plasmid and VSVg expression plasmid in HEK293 cells. The virus particles were harvested from the cell culture supernatants and concentrated by ultracentrifugation. The concentrated virus preparations were used to infect either mouse embryonic fibroblasts (MEF) or HEK293 cells which harbor both lacZ and firefly luciferase (Luc) reporter genes. Infection was monitored by the GFP signal which is expressed from the marker gene cassette of the viral vector. Under the conditions of this experiment, >98% of the test cells were GPF+ and thus were successfully transduced. The expression levels of lacZ and Luc reporter genes were measured by chemiluminescent assays using commercially available kits (lacZ assay kit from Roche and Luc from Promega). The lacZ siRNA virus only inhibited the expression of lacZ but not Luc. The specific inhibition was determined by the ratio of lacZ activity to Luc activity. The lacZ/Luc ratio of the uninfected parental cells was arbitrarily set to 1 and the values of the infected cells were calculated accordingly. As shown in FIG. 6, transfection with the virus resulted in dramatic reduction in the amount of expression of the lacZ gene in both MEK and HEK293 cells.

Figure 8:
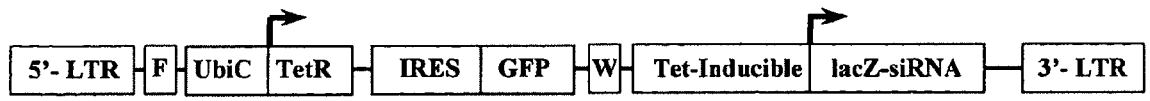
FIG. 8 shows a schematic illustration of a Tet-inducible lacZ siRNA lentiviral vector. A Tet repressor gene (TetR; SEQ ID NO: 5) is the under the control human UbiquitinC promoter and its expression can be monitored by the downstream GFP marker coupled by IRES element (internal ribosomal entry site). The anti-lacZ siRNA cassette is driven by a Tet-inducible pol III promoter derived from human U6-promoter (−328 to +1) containing a single TetR binding site (TetO1) between the PSE and TATA box (SEQ ID NO: 4). In the absence of tetracycline, TetR binds to the promoter and its expression is repressed. Upon the addition of tetracycline, TetR is moved from the promoter and transcription starts.

A tet-iducible lacZ siRNA lentiviral vector was also prepared as illustrated in FIG. 8. A Tet repressor gene (TetR; SEQ ID NO: 5) was placed the under the control of the human UbiquitinC promoter so that its expression could be monitored by the downstream GFP marker. The anti-lacZ siRNA cassette was driven by a Tet-inducible pol III promoter derived from human U6-promoter (−328 to +1) containing a single TetR binding site (TetO1) between the PSE and TATA box (SEQ ID NO: 4). The TetR coding sequence was PCR amplified from genomic DNA from the TOP10 strain of *E. coli* adn cloned into a modified version of FUIGW as a Bgl2-EcoR1 fragment. In the absence of tetracycline, TetR binds to the promoter and its expression is repressed. Upon the addition of tetracycline, TetR is moved from the promoter and transcription starts.

Figure 9:
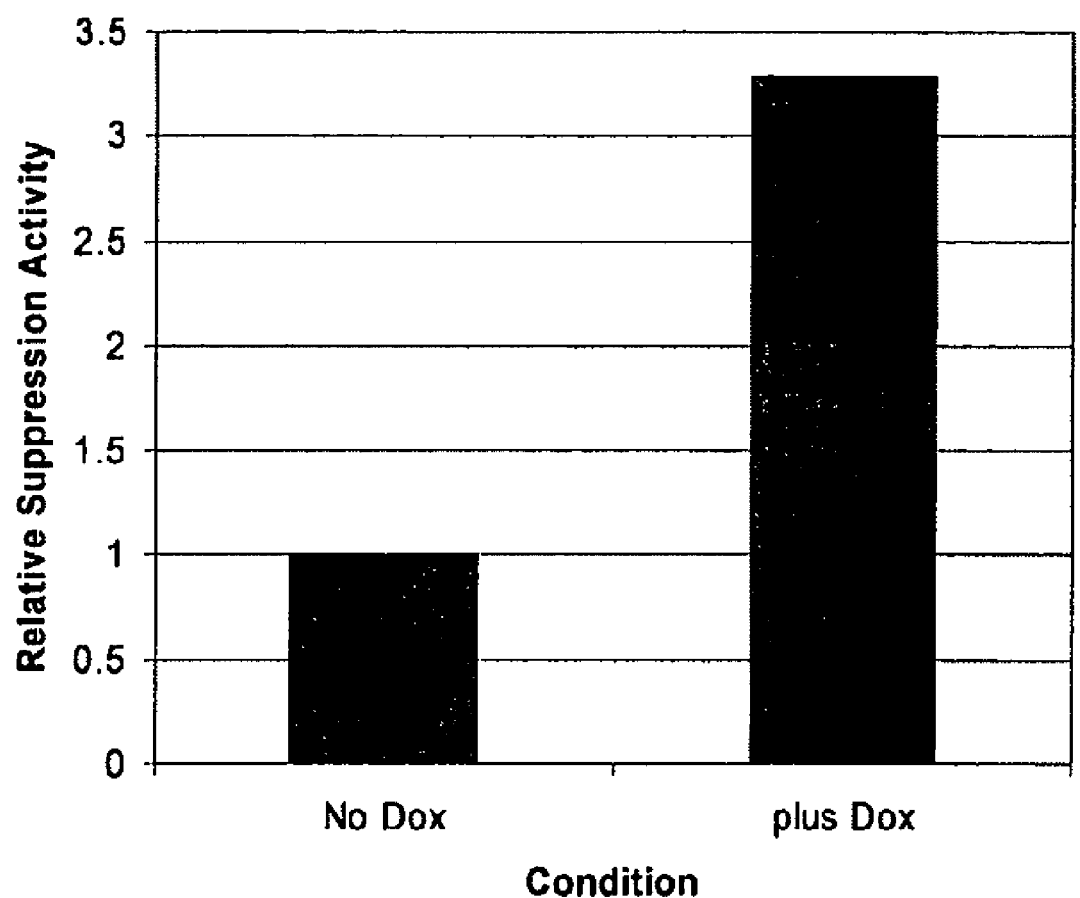
FIG. 9 shows the results of an experiment that demonstrated that a Tet-inducible siRNA expression cassette can regulate gene expression in response to Doxycycline treatment. lacZ and luciferase double expressing HEK293 cells (293Z+Luc) were transduced with a lentiviral vector carrying a Tet-inducible lacZ-siRNA cassette and a Tet repressor under the control of a UbiquitinC promoter (FIG. 8). The transduced cells were treated with 10 ug/ml Doxycycline (Plus Dox) for 48 hr or without the Doxycycline treatment as a control (No Dox). LacZ and luciferase activities were measured as described in the previous figures. The relative suppression activity is calculated as the ratio of lacZ versus luciferase and No Dox control was arbitrarily set to 1.

The Tet-inducible siRNA expression cassette was able to regulate gene expression in response to Doxycycline treatment. Virus was prepared from the retroviral construct carrying the Tet-inducible lacZ-siRNA cassette and a Tet repressor under the control of a UbiquitinC promoter and used to transduce HEK293 cells expressing both lacZ and luciferase (293Z+Luc). The transduced cells were treated with 10 ug/ml Doxycycline (Plus Dox) for 48 hr or without the Doxycycline treatment as a control (No Dox). LacZ and luciferase activities were measured as described in the previous figures. The relative suppression activity is calculated as the ratio of lacZ versus luciferase and No Dox control was arbitrarily set to 1. As can be seen in FIG. 9, in the presence of doxycycline suppression of lacZ activity was significantly enhanced.

Example 3

This example demonstrates the generation of transgenic animals that express an siRNA molecule encoded by a lentiviral vector. The expression of the lacZ specific siRNA described in Example 1 resulted in extensive suppression of lacZ activity in ROSA26+/− mice.

Figure 7:
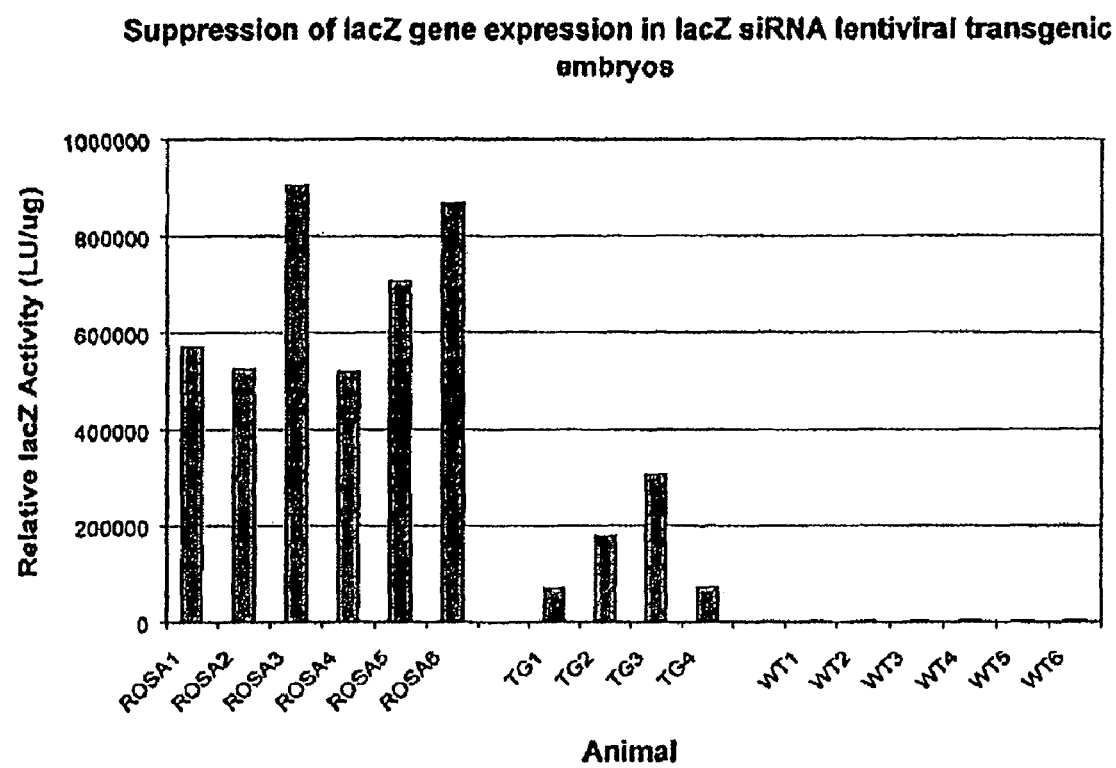
FIG. 7. Transgenic animals that express a lacZ specific siRNA molecule encoded by a lentiviral vector can successfully suppress the expression of the ubiquitous lacZ reporter gene in a ROSA26+/− background. ROSA1-6: the lacZ activities in the limb tissues of six E17.5 ROSA26+/− embryos which served as positive controls. The difference in lacZ activity between individual ROSA26+/− embryos may result from variable protein extraction efficiency. TG1-4: the lacZ activities in the limb tissues of four E17.5 transgenic embryos expressing a lentiviral vector-encoded lacZ siRNA molecule in ROSA+/− background. WT1-6: lacZ activity in the limb tissues of six E17.5 C57Bl/6 wildtype embryos, included as the negative control. The background levels of endogenous beta-galactosidase activity are general below 1,000 LU/ug, thus the columns are not visible.

ROSA26+/− mice carry only one copy of a ubiquitously expressed lacZ reporter gene. The lacZ siRNA virus preparations described in Example 2 were used for perivitelline injection of ROSA26+/− single cell embryos obtained from hormone primed C57Bl/6 female donors×ROSA26+/+ stud males. The injected single cell embryos were subsequently transferred into the oviduct of timed pseudopregnant female recipients. Embryonic day 15.5 to 17.5 (E15.5-17.5) fetuses were recovered from the surrogate mothers. Successful transgenesis was scored by positive GFP signal observed with the fetuses under fluorescent microscope. Protein extracts prepared from the limb tissues of the fetuses were used for the LacZ chemiluminescent assay according to the manufacturer's instruction (Roche), and protein concentrations of the tissue extracts were determined by the Bradford assay (Bio-Rad). The lacZ expression levels were expressed as light units (LU) per ug of proteins (LU/ug). The E15.5-17.5 fetuses from the timed mating of C57Bl/6 females×ROSA26+/+ males and C57Bl/6 females×C57Bl/6 males were served as the positive and negative controls respectively. The results are shown in FIG. 7. Animals G1-G4 (those treated derived from embroys infected with the virus comprising the siRNA construct) showed markedly decreased expression of the lacZ gene as compared with untreated control animals.

What is claimed is:

1. A method of expressing an siRNA within a cell, the method comprising:
 infecting a target hematopoietic stem or precursor cell ex vivo with the recombinant retrovirus,
 wherein the retroviral construct comprises the R and U5 sequences from a 5' lentiviral long terminal repeat (LTR), a self-inactivating lentiviral 3' LTR, an RNA polymerase III promoter region, and an RNA coding region encoding an siRNA operably linked to the RNA polymerase III promoter region;
 wherein the RNA polymerase III promoter region and the RNA coding region are located between the 5' LTR and the 3' LTR;
 wherein the RNA coding region encodes a self-complementary RNA molecule having a sense region, an antisense region and a loop region; and
 wherein the sense region and the antisense region are each between about 15 and about 30 nucleotides in length.

2. The method of claim 1, wherein the retroviral construct further comprises at least one termination sequence operably linked to the RNA coding region.

3. The method of claim 1, wherein the promoter region comprises a promoter, wherein the promoter is inducible.

4. The method of claim 3, wherein the inducible promoter is activated with tetracycline.

5. The method of claim 1, wherein the loop region is about 2 to about 10 nucleotides in length.

6. The method of claim 1, wherein expression of the RNA coding region results in the down regulation of a target gene.

7. The method of claim 1 wherein the 5' LTR sequences are from HIV.

8. The method of claim 1, wherein the self-inactivating 3' LTR is a modified HIV 3' LTR.

9. The method of claim 1, wherein the recombinant retrovirus is pseudotyped.

10. The method of claim 1, wherein the target cell is a hematopoietic stem cell.

11. The method of claim 1, wherein the target cell is a hematopoietic precursor cell.

12. The method of claim 1, wherein the target cell is CD34+.

13. A method of expressing an siRNA within a cell, the method comprising:
 infecting a target hematopoietic stem or precursor cell ex vivo with the recombinant retrovirus,
 wherein the retroviral construct comprises the R and U5 sequences from a 5' lentiviral long terminal repeat (LTR), a self-inactivating lentiviral 3' LTR, a first RNA coding region encoding a first siRNA strand operably linked to a first RNA polymerase III promoter, and a second RNA coding region encoding a second siRNA strand operably linked to a second RNA polymerase III promoter, wherein the second siRNA strand is substantially complementary to the first siRNA strand, wherein the first and second RNA polymerase III promoters and first and second RNA coding regions are located between the 5' LTR and the 3' LTR.

14. A method of expressing an siRNA within a cell, the method comprising:
 infecting a target hematopoietic stem or precursor cell ex vivo with the recombinant retrovirus,
 wherein the retroviral construct comprises the R and U5 sequences from a 5' lentiviral long terminal repeat (LTR), a self-inactivating lentiviral 3' LTR, an siRNA coding region, a first RNA polymerase III promoter, and a second RNA polymerase III promoter, wherein the first and second RNA polymerase III promoters are operably linked to the siRNA coding region such that expression of the siRNA coding region from the first RNA polymerase III promoter results in the synthesis of a first siRNA and expression of the siRNA coding region from the second RNA polymerase III promoter results in the synthesis of a second siRNA, wherein the first and second RNA polymerase III promoters and the siRNA coding regions are located between the 5' LTR and the 3' LTR.

* * * * *

UNITED STATES PATENT AND TRADEMARK OFFICE
CERTIFICATE OF CORRECTION

PATENT NO. : 8,361,787 B2
APPLICATION NO. : 12/795581
DATED : January 29, 2013
INVENTOR(S) : Carlos Lois-Caballe, David Baltimore and Xiao-Feng Qin Page 1 of 1

It is certified that error appears in the above-identified patent and that said Letters Patent is hereby corrected as shown below:

In the Specification

In Column 1 Lines 16-21, under GOVERNMENT SUPPORT, change:
"This invention was made with government support under Grant Number GM39458 awarded by the National Institutes of Health. The United States Government has certain rights in the invention."

To:
-- This invention was made with government support under Grant Nos. GM039458, AI039975, AI055281 awarded by the National Institutes of Health. The government has certain rights in the invention. --

Signed and Sealed this
Second Day of June, 2020

Andrei Iancu
*Director of the United States Patent and Trademark Office*